United States Patent
Stoddart et al.

(10) Patent No.: US 9,828,259 B2
(45) Date of Patent: Nov. 28, 2017

(54) EXCAGE: SYNTHESIS OF VIOLOGEN-LIKE PYRIDINIUM-BASED CAGES FOR THE SELECTIVE CAPTURE OF POLYCYCLIC AROMATIC HYDROCARBONS

(71) Applicants: Northwestern University, Evanston, IL (US); King Abdulaziz City for Science and Technology (KACST), Riyadh (SA)

(72) Inventors: James Fraser Stoddart, Evanston, IL (US); Edward J. Dale, Evanston, IL (US); Nicolaas A. Vermeulen, Indianapolis, IN (US); Jonathan C. Barnes, Waltham, MA (US); Michal Juricek, Basel (CH)

(73) Assignees: Northwestern University, Evanston, IL (US); King Abdulaziz City For Science and Technology (KACST) (SA)

( * ) Notice: Subject to any disclaimer, the term of this patent is extended or adjusted under 35 U.S.C. 154(b) by 11 days.

(21) Appl. No.: 14/844,577

(22) Filed: Sep. 3, 2015

(65) Prior Publication Data

US 2016/0229708 A1    Aug. 11, 2016

Related U.S. Application Data

(60) Provisional application No. 62/045,511, filed on Sep. 3, 2014.

(51) Int. Cl.
*C07D 401/14* (2006.01)
*C07D 213/06* (2006.01)
(Continued)

(52) U.S. Cl.
CPC ............ *C02F 1/285* (2013.01); *B01D 15/363* (2013.01); *C07D 213/06* (2013.01);
(Continued)

(58) Field of Classification Search
CPC ..... B01D 15/363; B01D 15/368; C02F 1/285; C02F 1/42; C02F 2001/422; C02F 2101/327; C07D 213/06; C07D 401/14
See application file for complete search history.

(56) References Cited

U.S. PATENT DOCUMENTS

2014/0179017 A1* 6/2014 Stoddart .............. C07D 471/22
436/140

OTHER PUBLICATIONS

Dale et al., "ExCage" Journal of the American Chemical Society, Jun. 26, 2014, 136, pp. 10669-10682.*

(Continued)

*Primary Examiner* — Lucas Stelling
(74) *Attorney, Agent, or Firm* — Klintworth & Rozenblat IP LLP

(57) ABSTRACT

Compounds are provided for the capture of polycyclic aromatic hydrocarbons. The compound is selected from formula (I) and formula (II):

(Continued)

Scheme (1)

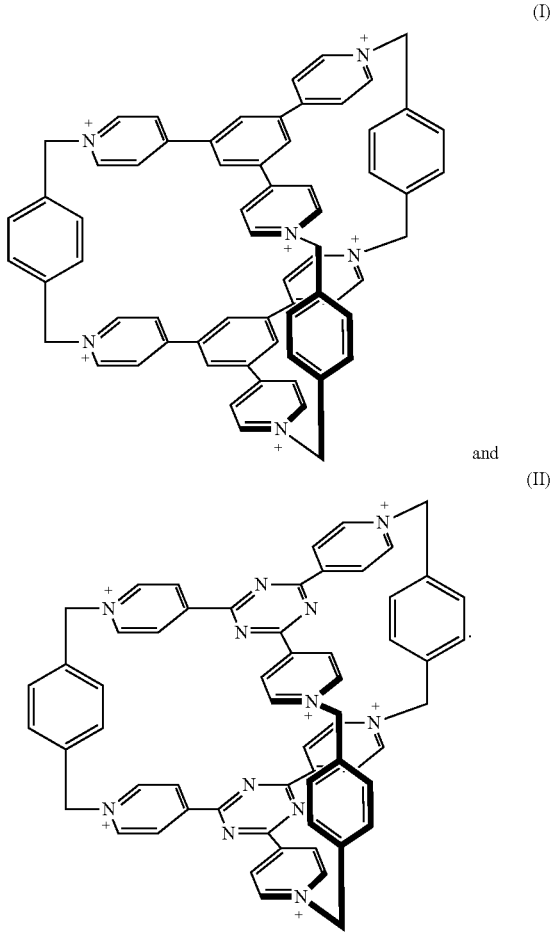

The compound includes a salt formed with a suitable counter anion.

6 Claims, 6 Drawing Sheets

(51) Int. Cl.
C02F 1/42 (2006.01)
C02F 1/28 (2006.01)
B01D 15/36 (2006.01)
C02F 101/32 (2006.01)

(52) U.S. Cl.
CPC .............. *C07D 401/14* (2013.01); *C02F 1/42* (2013.01); *C02F 2001/422* (2013.01); *C02F 2101/327* (2013.01)

(56) References Cited

OTHER PUBLICATIONS

Hafezi et al. "Modulating the Binding of Polycyclic Aromatic Hydrocarbons Inside a Hexacationic Cage by Anion-pi Interactions" Angewandte Chemie International Ed., 2015, 54, pp. 456-461. (first. pub. Nov. 19, 2014).*
Snyder et al. "Introduction to Modern Liquid Chromatography, Third Edition", 2010, Wiley & Sons, Inc., pp. 879-886.*
Anderson et al., "Expanding Roles for Templates in Synthesis," Acc. Chem. Res. 1993, 26:469-475.
Anderson et al., "Ligand binding by butadiyne-linked porphyrin dimers, trimers and tetramers," J. Chem. Soc. Perkin Trans. 1995, 2231-2245.
Barnes et al., "ExBox: A Polycyclic Aromatic Hydrocarbon Scavenger," J. Am. Chem. Soc. 2013, 135:183-192.
Barnes et al., "Synthesis of ExnBox Cyclophanes," J. Org. Chem. 2013, 78:11962-11969.
Bryant et al., "Spherands Contianing Cyclic Urea Units," J. Am. Chem. Soc. 1990, 12:5837-5843.
Cacciapaglia et al., "Catalysis by Metal Ions in Reactions of Crown Ether Substrates," Chem. Soc. Rev. 1993, 22:221-231.
Chen et al., "An EPR and NMR Study of Supramolecular Effects on Paramagnetic Interaction between a Nitroxide Incarcerated within a Nanocapsule iwth a Nitroxide in Bulk Aqueous Media," J. Am. Chem. Soc. 2008, 130:7206-7207.
Cram et al., "Shell Closure of Two Cavitands Forms Carcerand Complexes with Compounds of the Medium as Permanent Guests," J. Am. Chem. Soc. 1985, 107:2575-2576.
Cram et al., "Host-Guest Complexation. 35. Spherands, the First Completely Preorganized Ligand Systems," J. Am. Chem. Soc. 1985, 107:3645-3657.
Cram et al., "Host-Guest Complexation. 36. Spherand and Lithium and Sodium Ion Complexation Rates and Equilibria," J. Am. Chem. Soc. 1985, 107:3657-3668.
Cram et al., "Host-Guest Complexation. 47. Carcerands and Carcaplexes, the First Closed Molecular Container Compounds," J. Am. Chem. Soc. 1988, 110:2554-2560.
Cram, et al., "Guest Release and Capture by Hemicarcerands Introduces the Phenomenon of Constrictive Binding," J. Am. Chem. Soc. 1991, 113:7717-7727.
Cram, "Molecular container compounds," Nature 1992, 356:29-36.
Cram, "Hemicarcerands That Encapsulate Hydrocarbons with Molecular Weights Greater than Two Hundred," J. Am. Chem. Soc. 1993, 115:10111-10116.
Cram et al., "Container Molecules and Their Guests," in Monographs in Supramolecular Chemistry; Ed.Stoddart, J.F. Royal Society of Chemistry, Cambridge, 1997.
Crowley et al., "Active metal template synthesis of rotaxanes, catenanes and molecular shuttles," Chem. Soc. Rev. 2009, 38:1530-1542.
Dale et al., "ExCage," J. Am. Chem. Soc. 2014, 136:10669-10682.
Dietrich et al., "Les Cryptates," Tetrahedron Lett. 1969, 34:2889-2892.
Dietrich et al., "Cryptates—XI Complexes Macrobicycliques, Formation, Structure, Proprietes," Tetrahedron 1973, 29:1647-1658.
Giri et al., "Alkylated organic cages: from porous crystals to neat liquids," Chem. Sci. 2012, 3:2153-2157.
Gries et al., "Multi-Step Redox Systems, LVN—Quaternary Salts of Pyridyl-Substituted 1,3,5-Trizines—A New Class of Two- to Four-Step Reversible Redox Systems," Liebigs Ann. Chem. 1991, pp. 1021-1028.
Hafezi et al. "Modulating the binding of polycyclic aromatic hydrocarbons inside a hexacationic cage by anion-πinteractions," Angew. Chem. Int. Ed. Engl. 2015, 54:456-461.
Hao et al., "Photoinduced Catalytic Reaction by a Fluorescent Active Cryptand Containing an Anthracene Fragment," Angew. Chem. Int. Ed. 2010, 49:8148-8151.
Hoss et al., "Template Syntheses," Angew. Chem. Int. Ed. Engl. 1994, 33:375-384.
Huang et al., "Structure of K+(cryptand[2.2.2]) electride and evidence for trapped electron pairs," Nature 1988, 331:599-601.
Hubin et al., "Template routes to interlocked molecular structures and orderly molecular entanglements," Coord. Chem. Rev. 2000, 200:5-52.
Ihm et al., "Paired Carceroisomers," Angew. Chem. Int. Ed. 2006, 45:2056-2059.
Jasat et al., "Carceplexes and Hemicarceplexes," Chem. Rev. 1999, 99(4):931-967.
Juricek et al., "Ex2Box: Interdependent Modes of Binding in a Two-Nanometer-Long Synthetic Receptor," J. Am. Chem. Soc. 2013, 135:12736-12746.

(56) References Cited

OTHER PUBLICATIONS

Li et al., "Hemicarceplex Formation With a Cyclotriveratrylene-Based Molecular Cage Allows Isolation of High-Purity (≥99.0%) C70 Directly from Fullerene Extracts," org. lett. 2012, 14:6146-6149.

Lin et al., "Assembly of Water-Soluble, Dynamic, Covalent Container Molecules and Their Application in the Room-Temperature Stabilization of Protoadamantene," Chemistry 2012, 18:12864-12872.

Lopez et al., "Reversible Reduction of Oxygen to Peroxide Facilitated by Molecular Recognition," Science 2012, 335:450-454.

Lu et al., "Transient Innermolecular Carbene-Hemicarcerand Complex of Fluorophenylcarbene," J. Phys. Chem. A 2011, 115:13799-13803.

Makeiff et al.,"Template Effects in the Formation of a Tetramethylene-Bridged Hemicarceplex," J. Am. Chem. Soc. 2000, 122:1337-1342.

Makeiff et al., "A Six-Bowl Carceplex That Entraps Seven Guest Molecules," J. Am. Chem. Soc. 2005, 127:12363-12367.

Meyer et al., "Template-directed synthesis employing reversible imine bond formation," Chem. Soc. Rev. 2007, 36:1705-1724.

Mitjaville et al., "New and Efficient Syntheses of Symmetrical Phosphorus-containing Cryptands," J. Am. Chem. Soc. 1994, 116:2161-2162.

Roach et al., "The Room-Temperature Stabilization of Bicyclo[2.2.2]oct-1-ene and Bicyclo[3.2.1]oct-1-ene," Angew. Chem. Int. Ed. 2003, 42:3039-3043.

Rupar et al., "A Cryptand-Encapsulated Germanium(II) Dication," Science 2008, 322:1360-1364.

Schmittel et al, "Supramolecular Multicomponent Self-Assembly of Shape-Adaptive Nanoprisms: Wrapping up C60 with Three Porphyrin Units," Org. Lett. 2008, 10:2513-2516.

Sherman et al., "Carcerand Interiors Provide a New Phase of Matter," J. Am. Chem. Soc. 1989, 111:4527-4528.

Skowronek et al., "Chiral Iminospherand of a Tetrahedral Symmetry Spontaneously Assembled in a [6+4] Cyclocondensation," Org. Lett. 2008, 10:4755-4758.

Srinivasan et al., "Synthesis of nanoscale carceplexes from deep-cavity cavitands," Chem. Commun. 2008, 38:4640-4642.

von Hanisch et al., "Stepwise Synthesis and Coordination Compound of an Inorganic Cryptand," Angew. Chem. Int. Ed. 2007, 46:4775-4781.

Wang et al., "Reversible Photochemically Gated Transformation of a Hemicarcerand to a Carcerand," Angew. Chem. Int. Ed. 2013, 52:655-659.

Warmuth, "Recent Highlights in Hemicarcerand Chemistry," Acc. Chem. Res. 2001, 34:95-105.

Warmuth, "Photochemical and Thermal Reactions of Intermediates in the Phenylnitrene Rearrangement Inside a Hemicarcerand," J. Am. Chem. Soc. 2007, 129:1233-1241.

Wei et al., "A responsive supramolecular polymer formed by orthogonal metal-coordination and cryptand-based host-guest interaction," Chem. Commun. 2014, 50:3973-3975.

Yi et al., "Hydrogen Bonding-Induced Aromatic Oligoamide Foldamers as Spherand Analogues to Accelerate the Hydrolysis of Nitro-Substituted Anisole in Aqueous Media," J. Org. Chem. 2007, 72:870-877.

* cited by examiner (I)

(II)

(IIA)

EXCAGE: SYNTHESIS OF VIOLOGEN-LIKE PYRIDINIUM-BASED CAGES FOR THE SELECTIVE CAPTURE OF POLYCYCLIC AROMATIC HYDROCARBONS

CROSS-REFERENCE TO RELATED APPLICATIONS

This application claims benefit of priority under 35 U.S.C. 119 to U.S. provisional patent application Ser. No. 62/045,511, filed Sep. 3, 2014, and entitled "EXCAGE: SYNTHESIS OF VIOLOGEN-LIKE PYRIDINIUM-BASED CAGES FOR THE SELECTIVE CAPTURE OF POLYCYCLIC AROMATIC HYDROCARBONS," the contents of which are herein incorporated by reference in its entirety.

BACKGROUND

1. Technical Field

The present disclosure relates to pyridinium-based cages for the capture of polycyclic aromatic hydrocarbons.

2. Description of Related Art

Polycyclic aromatic hydrocarbons (PAHs or PAH compounds)—molecules which consist of two or more fused aromatic rings—are commonly found in natural crude oil deposits and also arise from anthropogenic processes during the incomplete combustion of carbon-based materials. The carcinogenic properties of PAHs have long been known and the pathways by which they cause mutagenesis are well documented. Not only are they prevalent in the environment, but they also persist on account of their low solubilities in water. The smaller PAHs, however, such as naphthalene, have a slightly higher water solubility and so are apt to leach out into the waterways. Yet, despite this situation, and its implications in relation to several disease states, naphthalene is produced annually on a massive scale. Although numerous hosts, with affinities for PAHs, based on dispersion forces and solvophobic effects, have been reported, the donor-acceptor interactions that have come into play with π-electron-deficient hosts, lead to higher binding affinities for PAHs, even in organic solvents. To date, few molecular compounds exist for eliminating PAHs from the environment.

N,N'-diazamacrobicyclic polyethers (cryptands) are three-dimensional analogues of the crown ethers. The N,N'-diazamacrobicyclic polyethers bind Group 1A and IIA metal cations so strongly that their 1:1 complexes became known as cryptates[1]. While the progression from crown ethers to cryptands occurred rapidly, it took quite a few years for the more highly designed spherands[2], carcerands[3] and hemicerands[4,5] to make their entry on to the scene as hosts with concave inner surfaces that provide convergent recognition sites for the complexation of guests in the form of ions and neutral molecules with divergent binding sites. These early developments in host-guest chemistry laid the foundations for the design and synthesis of cage-like host molecules with constitutions ranging from being wholly organic to metal-coordinated. These unnatural products, that fall under the umbrella of molecular cages, have been designed and synthesized for a vast range of different reasons including (i) exploring and exploiting their geometries, (ii) studying their properties as molecular magnets, (iii) employing them as molecular vehicles in the biomedical arena, and (iv) using them to modulate and catalyze chemical reactions.

Applicants reported[6] on the efficient template-directed synthesis' of higher homologues of cyclobis(paraquat-p-phenylene) (CBPQT$^{4+}$; FIG. 1: structure (I)), resulting from extending both its bipyridinium units by inserting a p-phenylene ring in a stepwise fashion between the two pyridinium rings to produce extended tetracationic cyclophanes of structure (II), denoted herein as Ex"Box$^{4+}$ where n=0-3 (FIG. 1: structure (II)). The tetracationic cyclophanes of structure (II) having n=1 is referenced herein as ExBox$^{4+}$ (FIG. 1: structure (IIA). These structures are referred to as "two-dimensional boxes" that bind poorly to PAHs; thus, there is a need for new compounds having greater binding affinity for PAHs.

BRIEF SUMMARY

In a first aspect, a compound selected from formula (I) and formula (II) is provided:

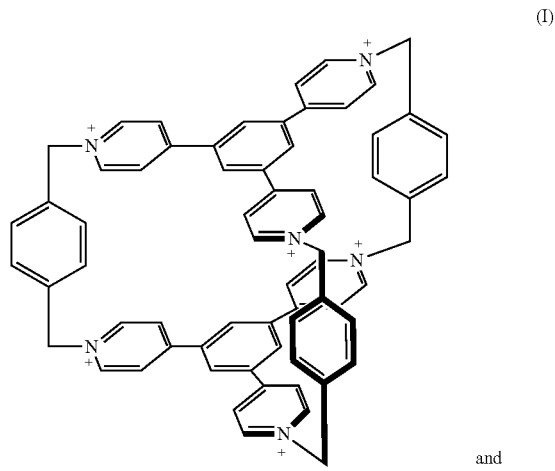

(I)

and

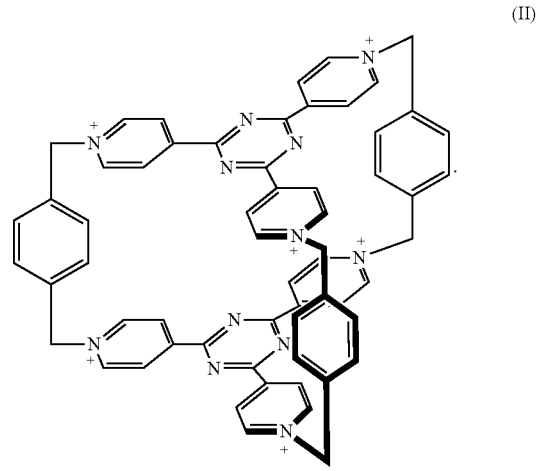

(II)

The compound includes a salt formed with a suitable counter anion.

In a second aspect, a method of separating a polycyclic aromatic hydrocarbon (PAH) compound from a solvent comprising the PAH compound is provided. The method includes the step of contacting the solvent comprising the PAH compound with a compound of formula (I) or (II):

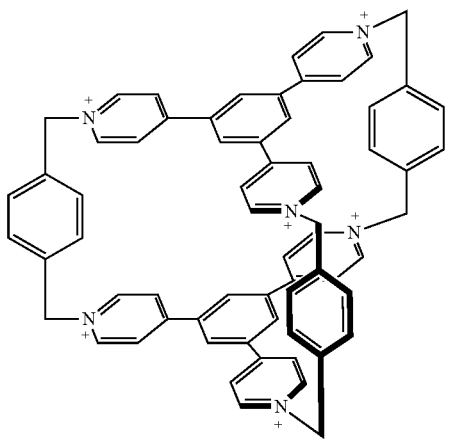

(I)

and

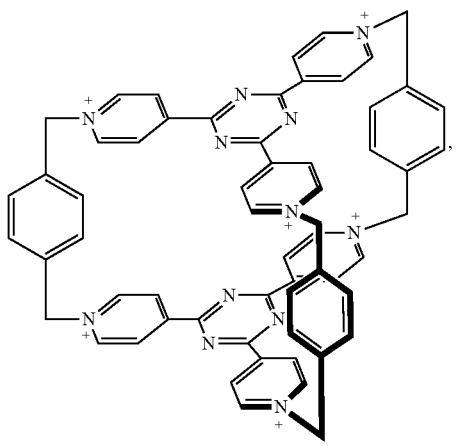

(II)

or a combination thereof. The compound includes a salt formed with a suitable counter anion.

In a third aspect, a method of separating a polycyclic aromatic hydrocarbon (PAH) compound from a solvent mixture is provided. The method includes several steps. The first step includes contacting the solvent mixture with a separation medium. The separation medium consists of a compound selected from formula (I) and (II):

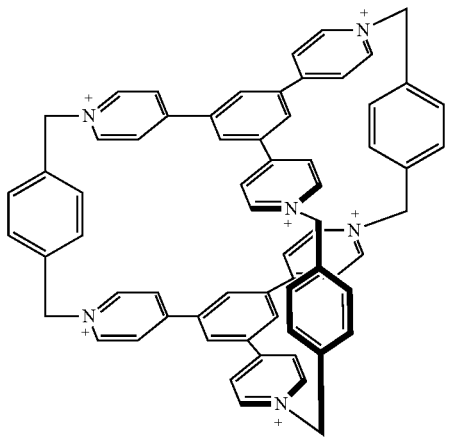

(I)

and

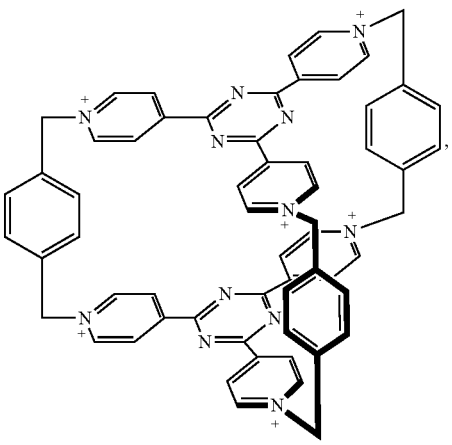

(II)

or a combination thereof. The compound comprises a salt formed with a suitable counter anion. The second step includes resolving the PAH compound from the solvent mixture using a liquid chromatography mobile phase. The third step includes isolating the PAH compound from the solvent mixture.

These and other features, objects and advantages of the present invention will become better understood from the description that follows. In the description, reference is made to the accompanying drawings, which form a part hereof and in which there is shown by way of illustration, not limitation, embodiments of the invention.

BRIEF DESCRIPTION OF THE DRAWINGS

The features, objects and advantages other than those set forth above will become more readily apparent when consideration is given to the detailed description below. Such detailed description makes reference to the following drawings.

Figure 1:
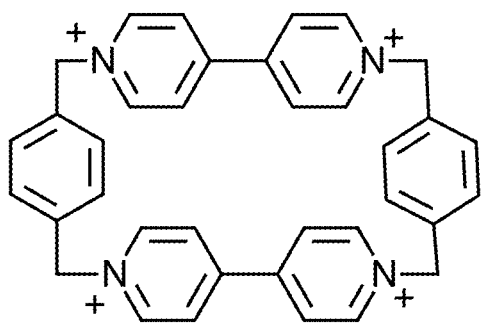
FIG. 1 depicts three exemplary prior art compounds having structures (I), (II) and (IIA).
Figure 1:
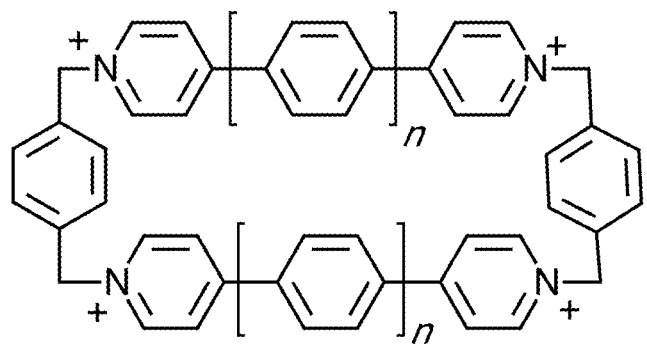
Figure 1:
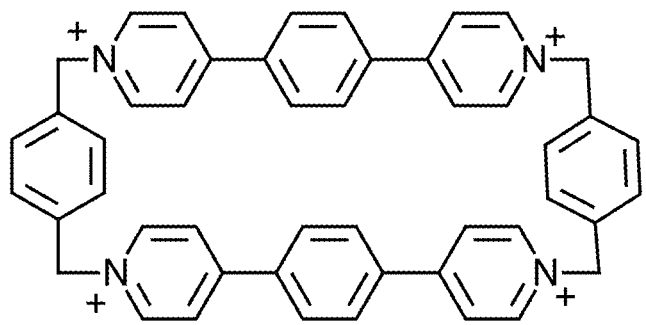

While the present invention is amenable to various modifications and alternative forms, exemplary embodiments thereof are shown by way of example in the drawings and are herein described in detail. It should be understood, however, that the description of exemplary embodiments is not intended to limit the invention to the particular forms disclosed, but on the contrary, the intention is to cover all modifications, equivalents and alternatives falling within the spirit and scope of the invention as defined by the embodiments above and the claims below. Reference should therefore be made to the embodiments and claims herein for interpreting the scope of the invention.

DETAILED DESCRIPTION

The compositions and methods now will be described more fully hereinafter with reference to the accompanying drawings, in which some, but not all permutations and variations of embodiments of the invention are shown. Indeed, the invention may be embodied in many different forms and should not be construed as limited to the embodiments set forth herein. These embodiments are provided in sufficient written detail to describe and enable one skilled in the art to make and use the invention, along with disclosure of the best mode for practicing the invention, as defined by the claims and equivalents thereof.

Likewise, many modifications and other embodiments of the compositions and methods described herein will come to mind to one of skill in the art to which the invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

Unless defined otherwise, all technical and scientific terms used herein have the same meaning as commonly understood by one of skill in the art to which the invention pertains. Although any methods and materials similar to or equivalent to those described herein can be used in the practice or testing of the present invention, the preferred methods and materials are described herein.

Moreover, reference to an element by the indefinite article "a" or "an" does not exclude the possibility that more than one element is present, unless the context clearly requires that there be one and only one element. The indefinite article "a" or "an" thus usually means "at least one."

As used herein, "about" means within a statistically meaningful range of a value or values such as a stated concentration, length, molecular weight, pH, sequence identity, time frame, temperature or volume. Such a value or range can be within an order of magnitude, typically within 20%, more typically within 10%, and even more typically within 5% of a given value or range. The allowable variation encompassed by "about" will depend upon the particular system under study, and can be readily appreciated by one of skill in the art.

Overview

Applicants made the seminal discovery of two novel compounds having improved binding affinity for PAHs. The advantages of these compounds include: (a) binding of PAHs is two or more orders of magnitude higher than analogous two-dimensional box structures; (b) anion exchange allows the compounds to function in the solid state, or solubilized in aqueous or organic media; and (c) binding of PAHs is selective. The applications of these compounds include: (a) filtration/sequestration of PAHs as low as two fused aromatic rings from anthropogenic sources: (b) capture of PAHs from an organic medium; (c) filtration of PAHs from the air; (d) capture of PAHs from an aqueous medium; (e) filtration/sequestration of PAHs from a complex mixtures of biologically significant molecules; and (f) detection of large PAHs in a colorimetric manner.

Compositions, Methods of Synthesis and Use as PAH Compound-Binding Media

In a first aspect, a bicyclic hexacationic cyclophane of formula (I) (designated herein as ExCage$^{6+}$) is provided by changing the constitution of the central 1,4-disubstituted benzenoid ring of ExBox$^{4+}$ to one that is 1,3,5-trisubstituted:

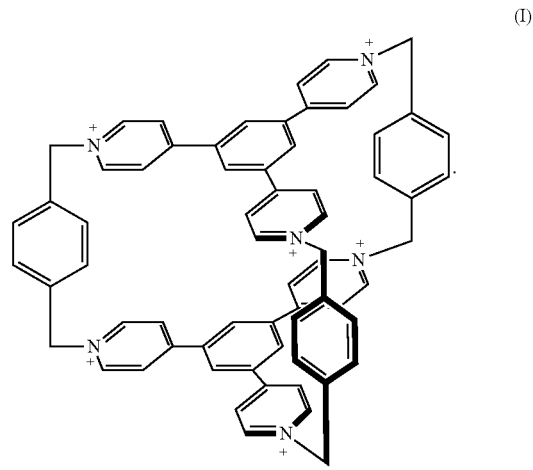

(I)

In a second aspect, a bicyclic hexacationic cyclophane of formula (II) (designated herein as BlueCage$^{6+}$) is provided by changing the constitution of the central 1,3,5-trisubstituted benzenoid ring of ExCage$^{6+}$ to one that is a 1,3,5-trisubstituted triazine ring:

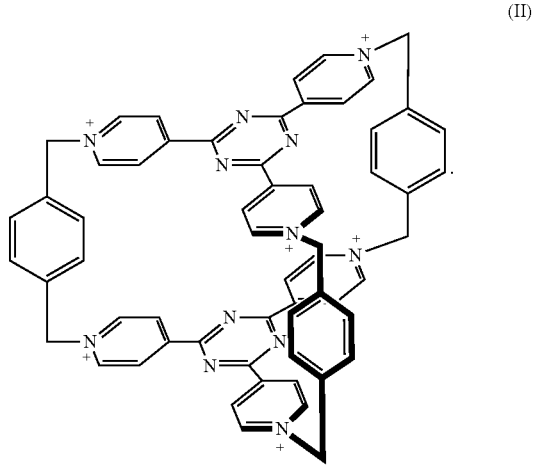

(II)

The synthesis (Scheme 1 (FIG. 2)) of ExCage.6PF$_6$ starts from 1,3,5-tris(4-pyridyl)benzene (TP) which was alkylated in MeCN/CH$_2$Cl$_2$ (2:1) under reflux for 3 days with an 15-fold excess of 1,4-bis(bromomethyl)benzene, affording the tribromide TB.3PF$_6$ in 75% yield, following counterion exchange (NH$_4$PF$_6$) in MeOH. Reaction of the tribromide with another equivalent of TP in MeCN in the presence of 0.3 equiv of tetrabutylammonium iodide (TBAI) as a catalyse[30] for 36 h at 80° C. afforded crude ExCage.6Cl, following the addition of TBACl to the reaction mixture to precipitate the crude product which, after preparative reverse-phase HPLC, was precipitated from the eluent with NH$_4$PF$_6$ to give ExCage.6PF$_6$ in 7% yield. In the absence of the catalyst only trace amounts of ExCage.6PF$_6$ were isolated. However, when the reaction was repeated in the presence of the catalyst, first of all employing phenanthrene (6 equiv) as a template and then pyrene (6 equiv), the yields were much improved. In both the template-directed syntheses with TBAI present, the reaction mixtures, following the addition of TBACl, had to be subjected to continuous liquid-liquid extraction with CHCl$_3$ in order to remove the templates, prior to being subjected to preparative reverse-phase chromatography, followed by counterion exchange by adding NH$_4$PF$_6$ to the eluent. Although the use of pyrene as a template raised the yield of ExCage.6PF$_6$ to 45%, the template proved somewhat difficult to remove by continuous liquid-liquid extraction while phenanthrene, which was easier to extract with CHCl$_3$, resulted in a 35% yield of the final product. In the absence of the catalyst, but in the presence of the templates, the yields of the reaction, carried out at room temperature for 21 days, were considerably less, namely, 9 and 11% using phenanthrene and pyrene, respectively.

The template-directed synthesis of BlueCage•6PF$_6$ was achieved by a procedure (Scheme 2 (FIG. 3)) similar to that described above for ExCage•6PF$_6$. Treatment of 2,4,6-tris(4-pyridyl)-1,3,5-triazine (TPT) with 10 equiv of 1,4-bis(bromo-methyl)benzene in MeCN/CH$_2$Cl$_2$ (1:1) heated at 90° C. for 3 days afforded TPTB in 58% yield following counterion exchange. The reaction of TPTB•3PF$_6$ with TPT in the presence of 6 equiv of phenanthrene as a template and 20 mol % of tetrabutylammonium iodide (TBAI) in MeCN at 90° C. for 3 days furnished phenanthrene ⊂ BlueCage.6Br, following precipitation of the crude product with tetrabutylammonium bromide (TBABr). Continuous extraction with CHCl$_3$ for 7 days, followed by preparative reverse-phase HPLC and anion exchange with aqueous NH$_4$PF$_6$, afforded BlueCage•6PF$_6$ as a white solid in 11% yield.

In one aspect, a separation medium is provided for isolating PAH compounds from a solvent comprising a PAH compound is provided. The separation medium comprises a bicyclic hexacationic cyclophane selected from formulas (I) and (II), or a combination thereof.

Figure 4:
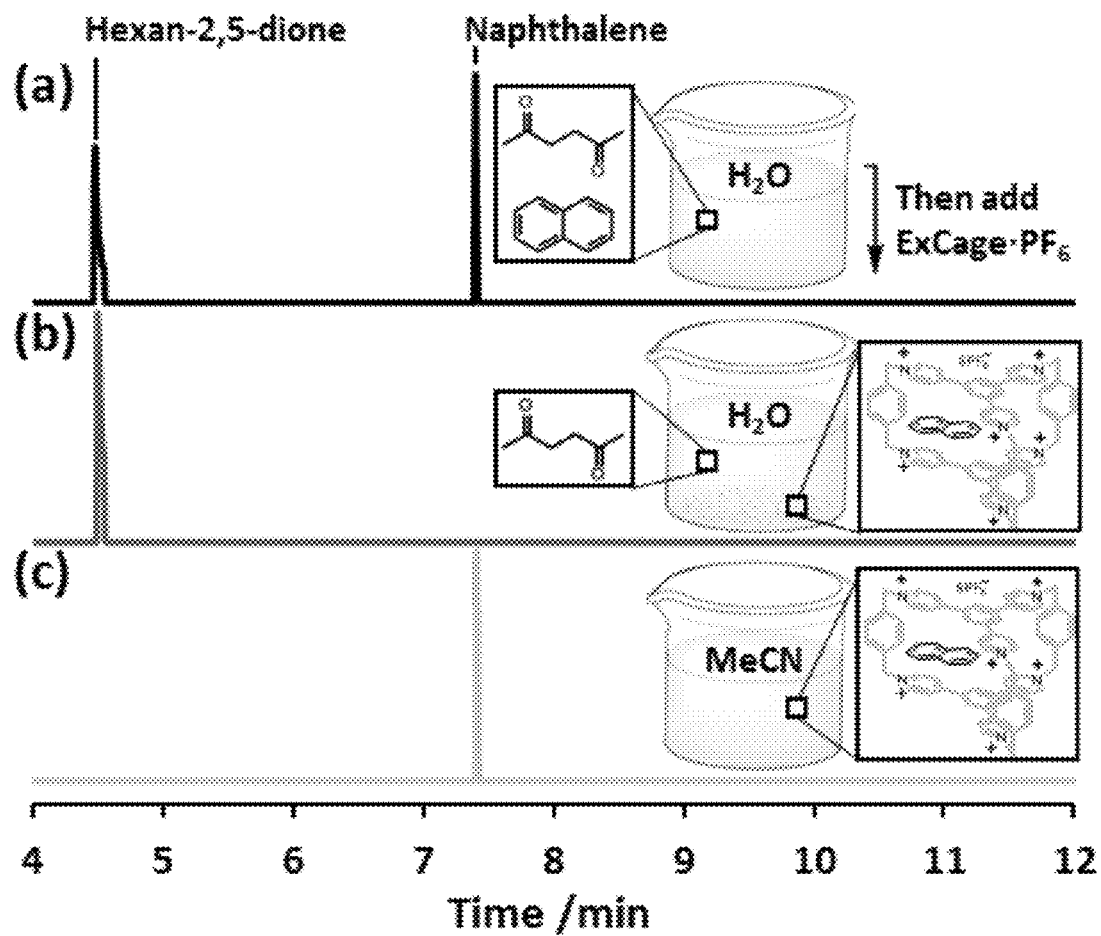
FIG. 4 depicts exemplary GC/MS traces showing the following: the outcomes when an aqueous saturated solution of naphthalene containing a small amount of hexan-2,5-dione as an internal standard (panel (a)); outcomes after adding ExCage$^{6+}$ as its insoluble PF$_6^-$ salt, sonicating, filtering off the solid, and injecting the solution into the GC/MS to reveal a trace containing only the internal standard, i.e., all the naphthalene has been scavenged from the saturated aqueous solution (panel (b)); and the result when the solid that was filtered off (above) is dissolved in MeCN and injected into the GC/MS, i.e., the peak for the naphthalene reappears and the internal standard is absent (panel (c)).

In another aspect, a method of separating a PAH compound from a solvent comprising a PAH compound is provided. Referring to FIG. 4, the method includes the step of contacting the solvent comprising a PAH compound with a compound of formula (I) or (II), or a combination thereof. Preferably, compound of formula (I) or (II) (or a combination thereof) is disposed as a stationary phase, wherein the stationary phase is in contact with the solvent comprising a PAH compound. The solvent can be either an aqueous or organic solvent. The stationary phase comprising a compound of formula (I) or (II) can be disposed preferably in a column for performing chromatographic separation of the PAH compound from solvent comprising a PAH compound. A preferred chromatographic separation for this purpose includes high performance liquid chromatography (HPLC). Since PAH compounds are generally hydrophobic, a preferred chromatography medium includes hydrophobic solvents, such as, for example, hexane.

Figure 5:
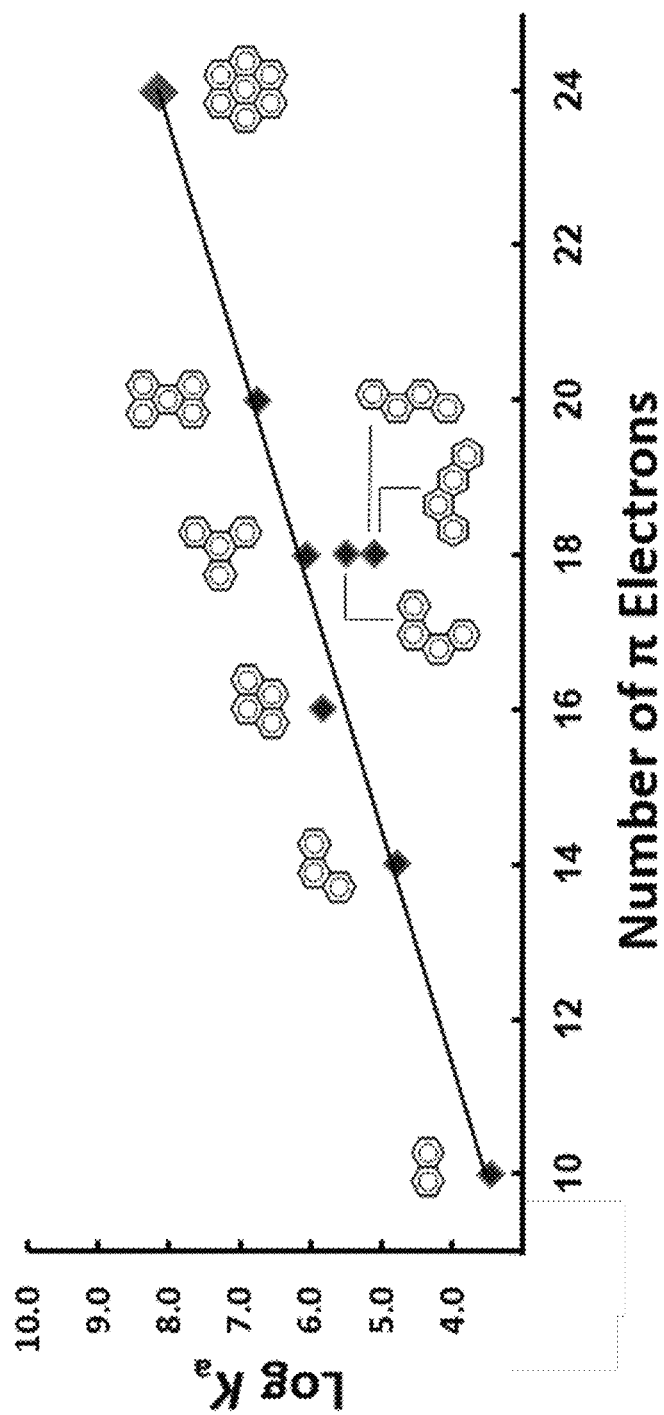
FIG. 5 depicts a linear plot of the binding affinities (log Ka's) in MeCN between ExCage$^{6+}$ and the number of π-electrons present in the eight PAHs, introduced in the previous figure, plus coronene (see the red diamond whose location is the result of a linear regression) for which there is no experimentally derived $K_a$ value on account of its lack of solubility in MeCN. Note that helicene, whose structure deviates from planarity, and tetraphene and chrysene, which have elongated constitutions, lie below the line.
Figure 6:
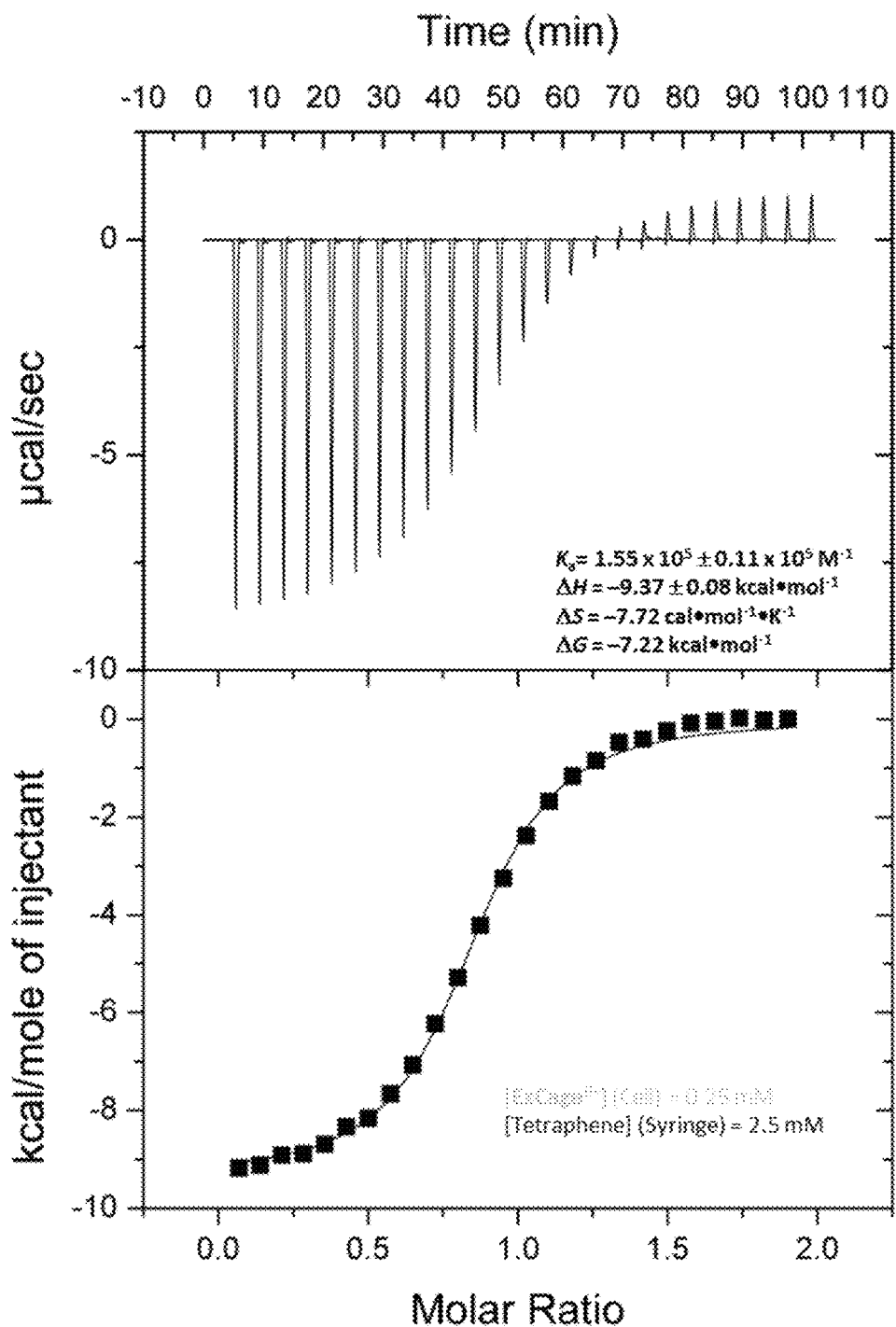
FIG. 6 depicts exemplary ITC data for the formation of tetraphene⊂ExCage$^{6+}$.

Preferred PAH compounds for separation include any planar polycyclic aromatic hydrocarbon. Exemplary PAH compounds amenable to high affinity binding with the compounds of formulas (I) and (II) include naphthalene, phenanthrene, tetraphene, chrysene, pyrene, helicene, triphenylene, perylene and coronene, among others (FIG. 5). The compounds of formulas (I) and (II) form 1:1 stoichiometric complexes with PAH compounds (see, for example, FIG. 6). In the case of the compound of formula (II), the type of anion can modulate binding of the compound to a PAH compound. For example, PF$_6^-$ anions mitigate PAH compound binding to the compound of formula (II), thereby resulting in lowered PAH compound binding affinity for the compound of formula (II) compared to formula (I) in solutions containing PF$_6^-$. This affect can be reversed by exchanging larger anions, such as BArF$^-$ anions, in place of PF$_6^-$ anions in solutions including the compound of formula (II), wherein compounds of formula (II) display comparable binding affinity as formula (I) for a given PAH compound.

The compounds of formulas (I) and (II) the can be used to detect large PAHs in a colorimetric manner. Evidence for detection of PAHs on a colorimetric nature can be seen in the color of the single crystalline compound-PAH complexes, such as those used to determine the constitution of complexes by X-ray diffraction. For example, while ExCage is colorless, the crystals resulting from complexation with tetraphene, pyrene, and perylene are yellow, orange and red, respectively. This color change is also observed in solution instantaneously upon combination of ExCage and specified PAH.

Without the claimed subject matter of the invention being bound to, or otherwise limited in any manner by, any particular theory, the mechanism of high binding affinity and retention of PAH compounds with the compounds of formulas (I) or (II) is based in part on then-electron deficiency of the compounds in addition to their three-dimensional bicyclic constitution.

Applications

In a first aspect, a compound selected from formula (I) and formula (II) is provided:

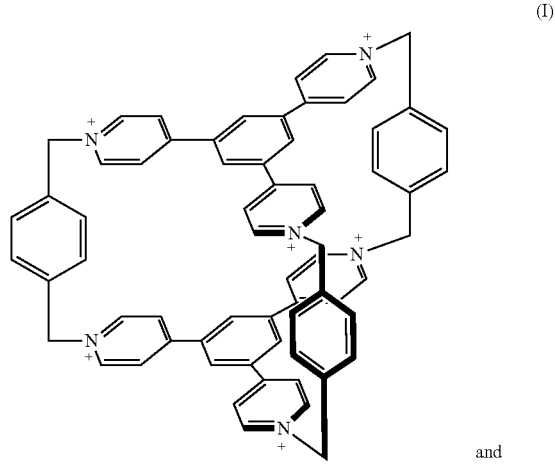

(I)

and

-continued (II)

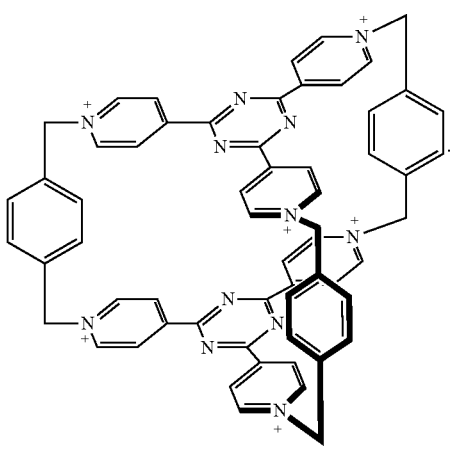

The compound comprises a salt formed with a suitable counter anion.

In a first respect of the first aspect, the compound consists of one having formula (I):

(I)

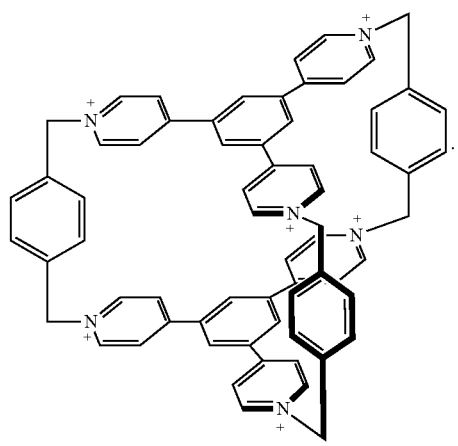

In a second respect of the first aspect, the compound consists of one having formula (II):

(II)

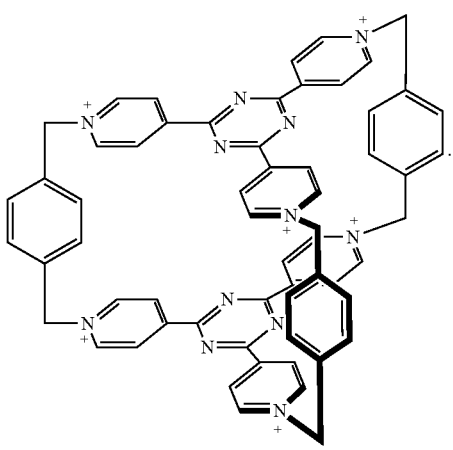

In a third respect of the first aspect, the suitable counter anion is selected from $PF_6^-$ and $BArF^-$.

In a second aspect, a separation medium consisting of a compound according the first aspect described above is provided. In one respect of this aspect, the separation medium includes a suitable counter anion selected from $PF_6^-$ and $BArF^-$.

In a third aspect, a method of separating a polycyclic aromatic hydrocarbon (PAH) compound from a solvent comprising the PAH compound is provided. The method includes the step of contacting the solvent comprising the PAH compound with a compound of formula (I) or (II):

(I)

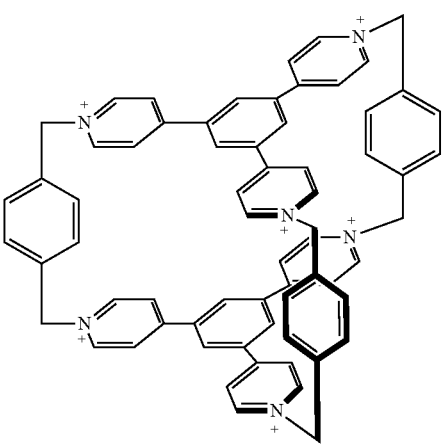

and (II)

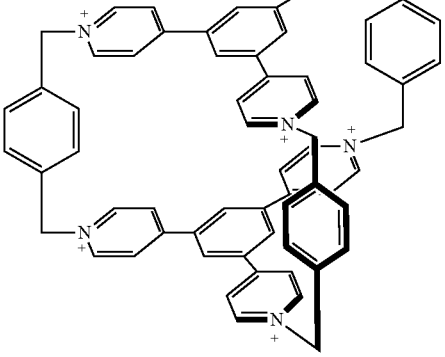

or a combination thereof.

The compound includes a salt formed with a suitable counter anion.

In a first respect, the method includes the compound having formula (I):

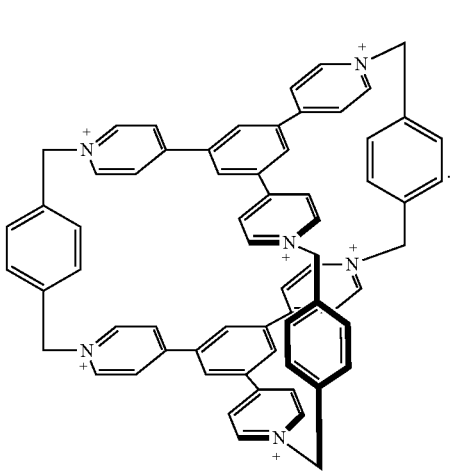

(I)

Alternatively, the method includes the compound having formula (II):

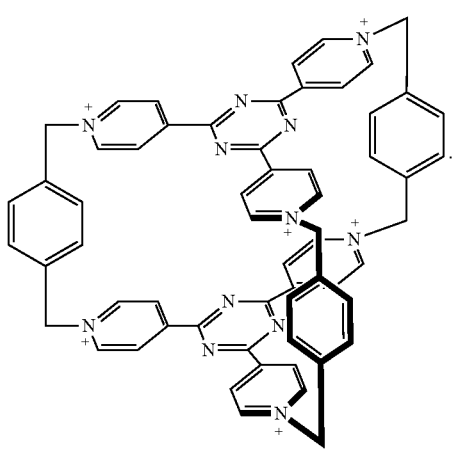

(II)

In these respects, the compound includes a suitable counter anion being selected from $PF_6^-$ and $BArF^-$. In these respects, the solvent is selected from an aqueous or organic solvent. In these respects, the PAH compound consists of a planar PAH compound. The PAH compound is selected from a group consisting of naphthalene, phenanthrene, tetraphene, chrysene, pyrene, helicene, triphenylene, perylene and coronene, or a combination thereof.

In a fourth aspect, a method of separating an polycyclic aromatic hydrocarbon (PAH) compound from a solvent mixture is provided. The method includes several steps. The first step includes contacting the solvent mixture with a separation medium. The second step includes resolving the PAH compound from the solvent mixture using a liquid chromatography mobile phase. The third step includes isolating the PAH compound from the solvent mixture. The separation medium consists of a compound selected from formula (I) and (II):

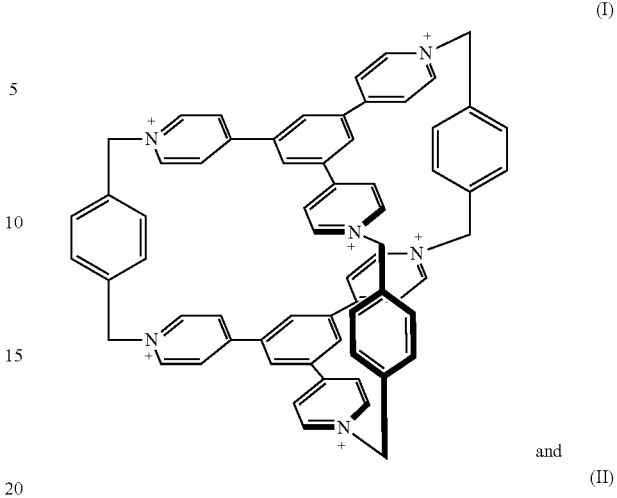

and

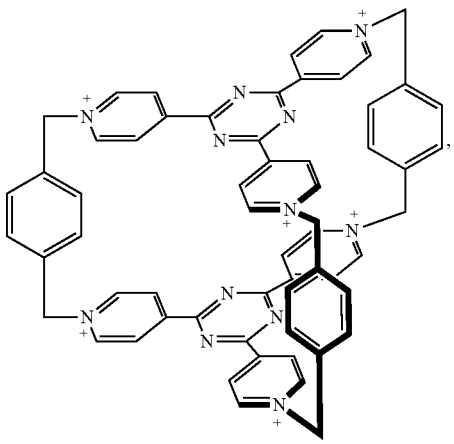

or a combination thereof. The compound comprises a salt formed with a suitable counter anion. In one respect, the method includes a compound wherein the suitable counter anion is selected from $PF_6^-$ and $BArF^-$. In another respect, the PAH compound is selected from naphthalene, phenanthrene, tetraphene, chrysene, pyrene, helicene, triphenylene, perylene and coronene, or a combination thereof. In another respect, the liquid chromatography mobile phase comprises hexane. In another respect, the separation medium is disposed in a chromatography column. In this respect, the chromatography column is configured for high performance liquid chromatography.

EXAMPLES

The invention will be more fully understood upon consideration of the following non-limiting examples, which are offered for purposes of illustration, not limitation.

Example 1. Materials and Methods

All reagents were purchased from commercial suppliers and used without further purification unless stated otherwise. 2,4,6-Tris(4-pyridyl)-1,3,5-triazine[8] and 2,4,6-tris(benzyl)pyridinium-4-yl)-1,3,5-triazine tris(hexafluorophosphate)[9] were synthesized as reported previously in the literature. Solvents were deoxygenated by passing Ar through the solvent for 30 min. 1,3,5-tris(4-pyridyl)benzene was synthesized as previously reported.[10] Analytical high-performance liquid chromatography (HPLC) was performed on reverse-phase HPLC (RP-HPLC) instruments, using a $C_{18}$-column and a binary solvent system (MeCN and $H_2O$ with 0.1% $CF_3CO_2H$). UV/Vis/NIR absorbance spectra were recorded using a UV-3600 Shimadzu spectrophotometer. Nuclear magnetic resonance (NMR) spectra were recorded on a BrukerAvance 600, Varian P-Inova 500, and Bruker F500 spectrometers, with working frequencies of 600, 500, and 500 MHz, respectively ($^1H$ NMR), and 150, 125, and 125 MHz, respectively ($^{13}C$ NMR). Chemical shifts are reported in ppm relative to the signals corresponding to the residual non-deuterated solvents ($CD_3CN$: $\delta_H$=1.94 ppm and $\delta_C$=1.32 and 118.26 ppm; DMF-$d_7$: $\delta_H$=8.03, 2.92, and 2.75 ppm and $\delta_C$=29.76, 34.89, and 163.15 ppm). High-resolution mass spectra (HRMS) were measured on an Agilent 6210 Time of Flight (TOF) LC-MS, using an ESI source, coupled with Agilent 1100 HPLC stack, using direct infusion (0.6 mL/min). Isothermal titration calorimetry (ITC) experiments were performed on a MicroCal system, VP-ITC model. A solution of ExCage.6PF$_6$ in MeCN was used as the host solution in a 1.8 mL cell. Solutions of PAHs in MeCN were added by injecting successively 10 μL of titrant over 20 s (25×) with a 300 s interval between each injection. Thermodynamic information was calculated using a one-site binding model utilizing data from which the heat of dilution of the guest was subtracted, with the average of triplicate runs reported. Cyclic voltammetry (CV) experiments were carried out at room temperature in argon-purged solutions of DMF with a Gamry Multipurpose instrument (Reference 600) interfaced to a PC. All CV experiments were performed using a glassy carbon working electrode (0.071 cm$^2$). The electrode surface was polished routinely with 0.05 μm alumina-water slurry on a felt surface immediately before use. The counter electrode was a Pt coil and the reference electrode was a Ag/AgCl electrode. The concentration of the sample and supporting electrolyte, tetrabutylammonium hexafluorophosphate (TBAPF$_6$), were 1.0 mM and 0.10 M, respectively. The CV cell was dried in an oven immediately before use, and argon was flushed continually through the cell as it was cooled down to room temperature to avoid condensation of water.

Example 2. Synthetic Protocols for Preparing the Compound of Formula (I)

Figure 2:
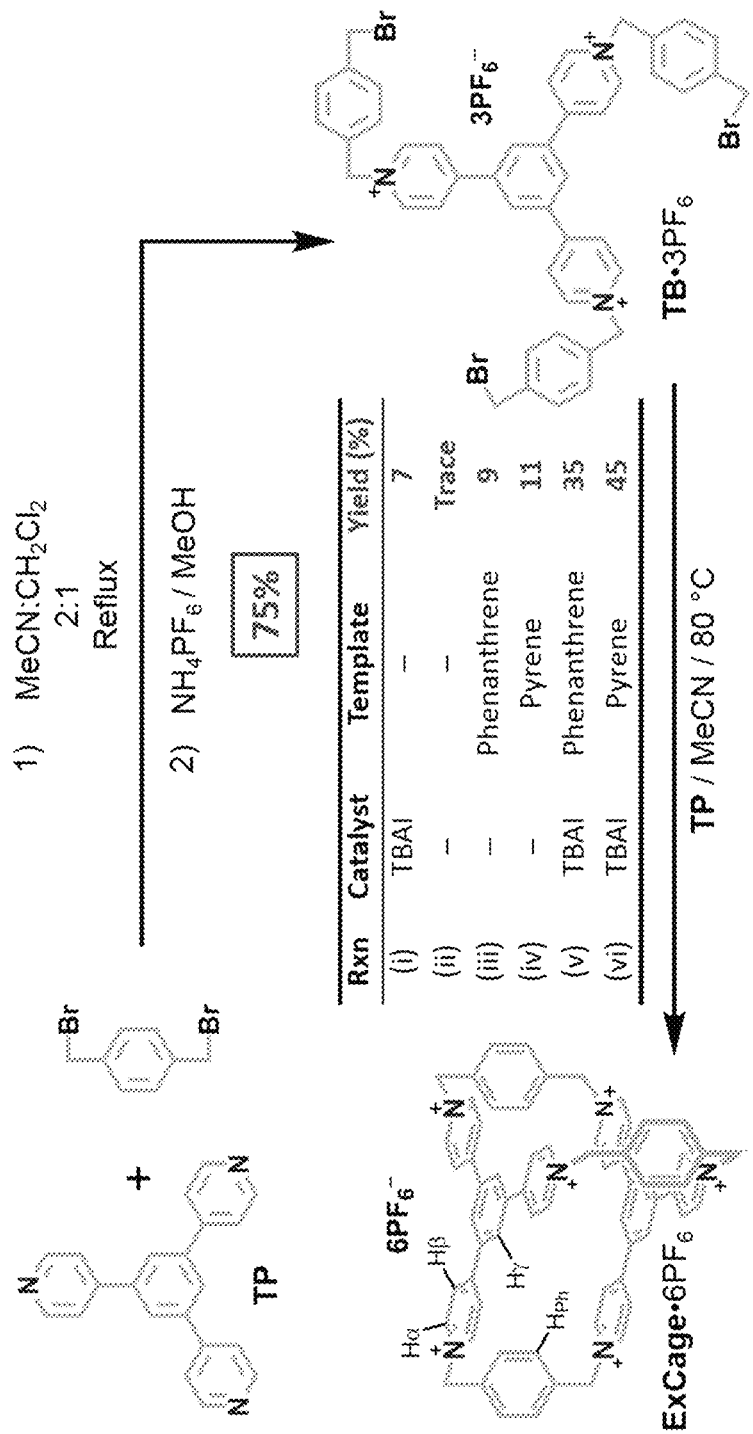
FIG. 2 depicts an exemplary scheme for the synthesis of ExCage 6PF$_6$.

Scheme (1) presented in FIG. 2 provides an overview of the synthesis of the compound of formula (I).

1) 1,3,5-(1-Methylpyridinium-4-yl)benzene Tris(hexafluorophosphate)—TM.3PF$_6$

The synthesis of TM.3PF$_6$ was achieved according to Scheme (1A):

(Scheme (1A))

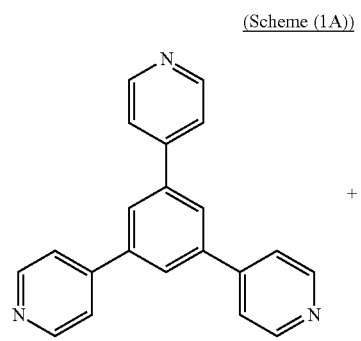

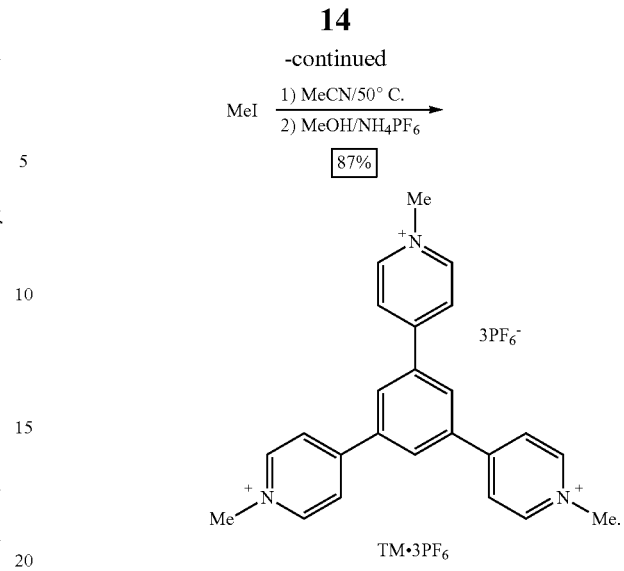

TM.3PF$_6$: A mixture of 1,3,5-tris(4-pyridyl)benzene (25.0 mg, 0.08 mmol) and MeI (150 μL, 2.40 mmol) in MeCN (5.0 mL) was heated at 50° C. while stirring for 18 h. The reaction mixture was cooled to room temperature and the precipitate was collected by filtration. The solid was dissolved in MeOH (50 mL) followed by the addition of NH$_4$PF$_6$ and dilution in H$_2$O (50 mL), resulting in the precipitation of pure TM.3PF$_6$ (55.5 mg, 87%) that was collected by filtration as a colorless solid. HRMS-ESI for TM.3PF$_6$; Calcd for $C_{24}H_{24}Br_3F_{12}N_3P_2$: m/z=644.1249 [M-PF$_6$]$^+$. Found: 644.1262 [M-PF$_6$]$^+$. $^1$H NMR (500 MHz, CD$_3$CN, ppm): $\delta_H$ 8.77 (AA' of AA'XX', J=6.9 Hz, 6H), 8.53 (s, 3H), 8.45 (XX' of AA'XX', J=7.0 Hz, 6H), 4.36 (s, 9H. $^{13}$C NMR (125 MHz, CD$_3$CN, ppm): $\delta_C$ 154.8, 146.6, 137.7, 131.6, 126.6, 48.9.

2) 1,3,5-(1-(4-Bromomethylbenzyl)pyridinium-4-yl)benzene

The synthesis of TB.3PF$_6$ was achieved according to Scheme (1B):

(Scheme (1B))

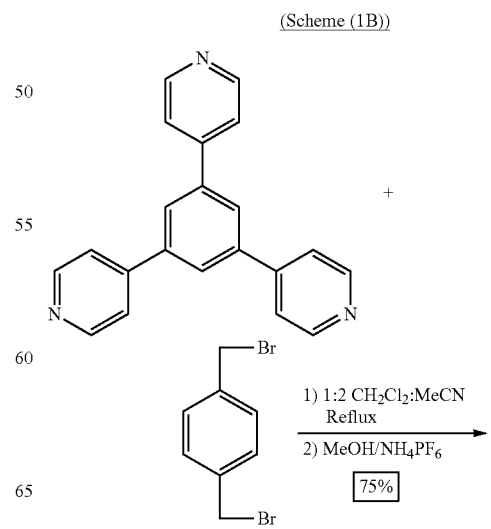

-continued

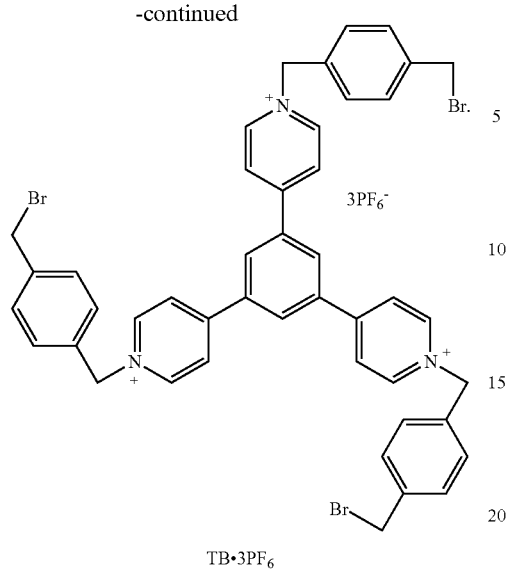

TB·3PF$_6$

Tris(hexafluorophosphate)—TB.3PF$_6$

TB.3PF$_6$: α,α'-Dibromo-p-xylene (8.96 g, 33.9 mmol) was added to MeCN/CH$_2$Cl$_2$ (1:1 v/v, 113 mL) and the suspension was heated at 60° C. until all of compound had dissolved. The temperature of the solution was raised to 90° C. and a suspension of 1,3,5-tris(4-pyridyl)benzene (TP) (700 mg, 2.26 mmol) in MeCN (37 mL) was added in aliquots during 2 h. After heating under reflux for 3 d, the reaction mixture was cooled to room temperature and the precipitate was diluted in CH$_2$Cl$_2$ (500 mL) and collected by filtration. The precipitate was dissolved in MeOH (100 mL), followed by the addition of an excess of NH$_4$PF$_6$ in H$_2$O (400 mL), resulting in the precipitation of pure TB.3PF$_6$ (2.19 g, 75%) that was collected by filtration as a colorless solid. $^1$H NMR (500 MHz, CD$_3$CN, ppm): δ$_H$ 8.90 (AA' of AA'XX', J=6.9 Hz, 6H), 8.53 (s, 3H), 8.49 (XX' of AA'XX', J=6.9 Hz, 6H), 7.55 (AA' of AA'BB', J=8.3 Hz, 6H), 7.49 (BB' of AA'BB', J=8.2 Hz, 6H), 5.78 (s, 6H), 4.61 (s, 6H). $^{13}$C NMR (125 MHz, CD$_3$CN, ppm): δ$_C$ 155.9, 145.8, 141.3, 137.7, 134.1, 132.0, 131.1, 130.5, 127.4, 64.6, 33.5. HRMS-ESI for TB.3PF$_6$; Calcd for C$_{45}$H$_{39}$Br$_3$F$_{12}$N$_3$P$_2$: m/z=1149.9952 [M-PF$_6$]$^+$. Found: 1149.9959 [M-PF$_6$]$^+$.

3) Cyclobis(1,3,5-tris(1,1'-(1,4-phenylenebis(methylene))-pyridinium-4-yl)benzene)-hexakis(hexafluorophosphate)—ExCage.6PF$_6$ The synthesis of ExCage.6PF$_6$ was achieved according to Scheme (1C):

(Scheme (1C))

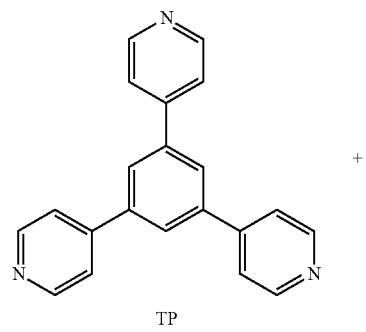

TP

+

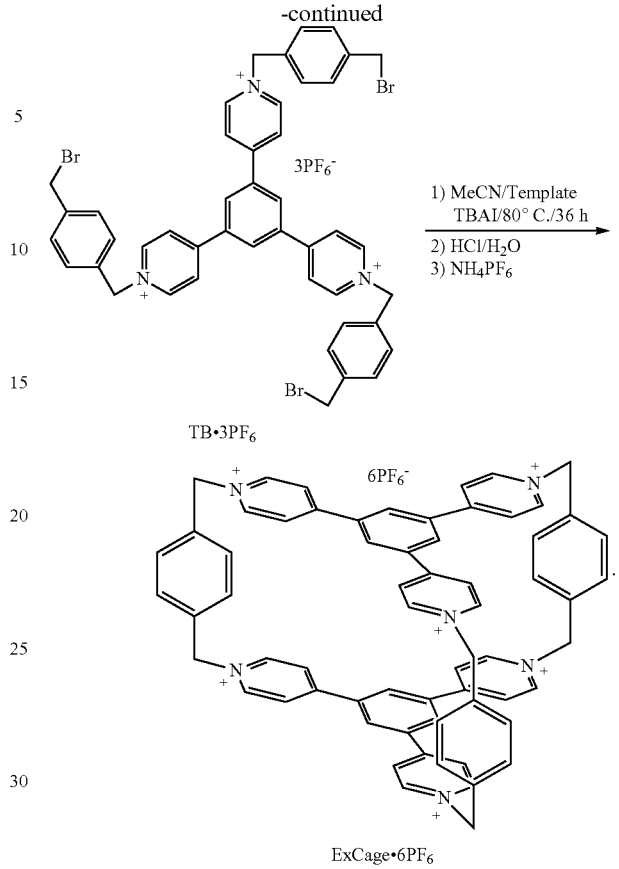

TB·3PF$_6$

1) MeCN/Template TBAI/80° C./36 h
2) HCl/H$_2$O
3) NH$_4$PF$_6$

ExCage·6PF$_6$

ExCage.6PF$_6$: Six reactions were carried out using different sets of conditions as follows: (i) catalyst with no template, (ii) no catalyst and no template, (iii) no catalyst and phenanthrene as template, (iv) no catalyst and pyrene as template, (v) catalyst and phenanthrene as template, and (vi) catalyst and pyrene as template.

(i) Catalyst with No Template.

A solution of TB.3PF$_6$ (150 mg, 0.129 mmol), TP (39.7 mg, 0.129 mmol), and tetrabutylammonium iodide (TBAI, 14.2 mg, 0.0383 mmol) in dry MeCN (50 mL) was heated at 80° C. for 36 h. The reaction was quenched by addition of an excess of TBACl, whereupon the crude product precipitated from solution as the hexachloride salt, which was dissolved in the minimum amount of H$_2$O/EtOH (19:1, v/v) before being subjected to high-performance reverse-phase preparative C$_{18}$ column chromatography, starting with H$_2$O containing 0.1% TFA as eluent, and adding up to 25% of MeCN/0.1% TFA. The chromatographically pure compound was precipitated by adding NH$_4$PF$_6$ to the eluent, affording pure ExCage.6PF$_6$ (15 mg, 7%). $^1$H NMR (500 MHz, CD$_3$CN, ppm): δ$_H$ 8.74 (AA' of AA'XX', J=7.0 Hz, 12H), 8.40 (s, 6H), 8.28 (XX' of AA'XX', J=6.6 Hz, 12H), 7.57 (s, 12H), 5.73 (s, 12H). $^{13}$C NMR (125 MHz, CD$_3$CN, ppm): δ$_C$ 154.2, 145.3, 136.9, 136.7, 131.6, 131.4, 126.5, 64.7. HRMS-ESI for ExCage.6PF$_6$; Calcd for C$_{66}$H$_{54}$F$_{24}$N$_6$P$_4$: m/z=755.1483 [M-2PF$_6$]$^{2+}$. Found: 755.1505 [M-2PF$_6$]$^{2+}$.

(ii) No Catalyst and No Template.

A solution of TB.3PF$_6$ (150 mg, 0.129 mmol), and TP (39.7 mg, 0.129 mmol) in dry MeCN (50 mL) was stirred at room temperature for 21 days. The reaction was quenched by addition of an excess of TBACl, whereupon the crude product precipitated from solution as the hexachloride salt, which was dissolved in the minimum amount of H$_2$O/EtOH (19:1, v/v) before being subjected to high-performance reverse-phase preparative C$_{18}$ column chromatography, starting with H$_2$O containing 0.1% TFA as eluent, and adding up to 25% of MeCN/0.1% TFA. The chromatographically pure compound was precipitated by adding NH$_4$PF$_6$ to the eluent, affording trace amounts of pure ExCage.6PF$_6$.

(iii) No Catalyst and Phenanthrene as Template.

A solution of TB.3PF$_6$ (150 mg, 0.129 mmol), TP (39.7 mg, 0.129 mmol), and phenanthrene (138 mg, 0.774 mmol) in dry MeCN (50 mL) was stirred at room temperature for 21 days. The reaction was quenched by addition of an excess of TBACl, whereupon the crude product precipitated from solution as the hexachloride salt, dissolved in H$_2$O, and template removed by continuous liquid-liquid extraction with CHCl$_3$ over the course of 3 days. The aqueous phase was concentrated and dissolved in the minimum amount of H$_2$O/EtOH (19:1, v/v) before being subjected to high-performance reverse-phase preparative C$_{18}$ column chromatography, starting with H$_2$O containing 0.1% TFA as eluent, and adding up to 25% of MeCN/0.1% TFA. The chromatographically pure compound was precipitated by adding NH$_4$PF$_6$ to the eluent, affording pure ExCage.6PF$_6$ (21 mg, 9%).

(iv) No Catalyst and Pyrene as Catalyst.

A solution of TB.3PF$_6$ (150 mg, 0.129 mmol), TP (39.7 mg, 0.129 mmol), and pyrene (156 mg, 0.774 mmol) in dry MeCN (50 mL) was stirred at room temperature for 21 days. The reaction was quenched by addition of an excess of TBACl, whereupon the crude product precipitated from solution as the hexachloride salt, dissolved in H$_2$O, and template removed by continuous liquid-liquid extraction with CHCl$_3$ over the course of 30 days. The aqueous phase was concentrated and dissolved in the minimum amount of H$_2$O/EtOH (19:1, v/v) before being subjected to high-performance reverse-phase preparative C$_{18}$ column chromatography, starting with H$_2$O containing 0.1% TFA as eluent, and adding up to 25% of MeCN/0.1% TFA. The chromatographically pure compound was precipitated by adding NH$_4$PF$_6$ to the eluent, affording pure ExCage.6PF$_6$ (26 mg, 11%).

(v) Catalyst and Phenanthrene as Template.

A solution of TB.3PF$_6$ (150 mg, 0.129 mmol), TP (39.7 mg, 0.129 mmol), TBAI (14.3 mg, 0.039 mmol), and phenanthrene (138 mg, 0.774 mmol) in dry MeCN (50 mL) was heated at 80° C. for 36 h. The reaction was quenched by addition of an excess of TBACl, whereupon the crude product precipitated from solution as the hexachloride salt, dissolved in H$_2$O, and template removed by continuous liquid-liquid extraction with CHCl$_3$ over the course of 3 days. The aqueous phase was concentrated and dissolved in the minimum amount of H$_2$O/EtOH (19:1, v/v) before being subjected to high-performance reverse-phase preparative C$_{18}$ column chromatography, starting with H$_2$O containing 0.1% TFA as eluent, and adding up to 25% of MeCN/0.1% TFA. The chromatographically pure compound was precipitated by adding NH$_4$PF$_6$ to the eluent, affording pure ExCage.6PF$_6$ (81 mg, 35%).

(vi) Catalyst and Pyrene as Template.

A solution of TB.3PF$_6$ (150 mg, 0.129 mmol), TP (39.7 mg, 0.129 mmol), TBAI (14.3 mg, 0.039 mmol), and pyrene (156 mg, 0.774 mmol) in dry MeCN (50 mL) was heated at 80° C. for 36 h. The reaction was quenched by addition of an excess of TBACl, whereupon the crude product precipitated from solution as the hexachloride salt, dissolved in H$_2$O, and template removed by continuous liquid-liquid extraction with CHCl$_3$ over the course of 30 days. The aqueous phase was concentrated and dissolved in the minimum amount of H$_2$O/EtOH (19:1, v/v) before being subjected to high-performance reverse-phase preparative C$_{18}$ column chromatography, starting with H$_2$O containing 0.1% TFA as eluent, and adding up to 25% of MeCN/0.1% TFA. The chromatographically pure compound was precipitated by adding NH$_4$PF$_6$ to the eluent, affording pure ExCage.6PF$_6$ (105 mg, 45%).

Example 3. Synthetic Protocols for Preparing the Compound of Formula (II)

Figure 3:
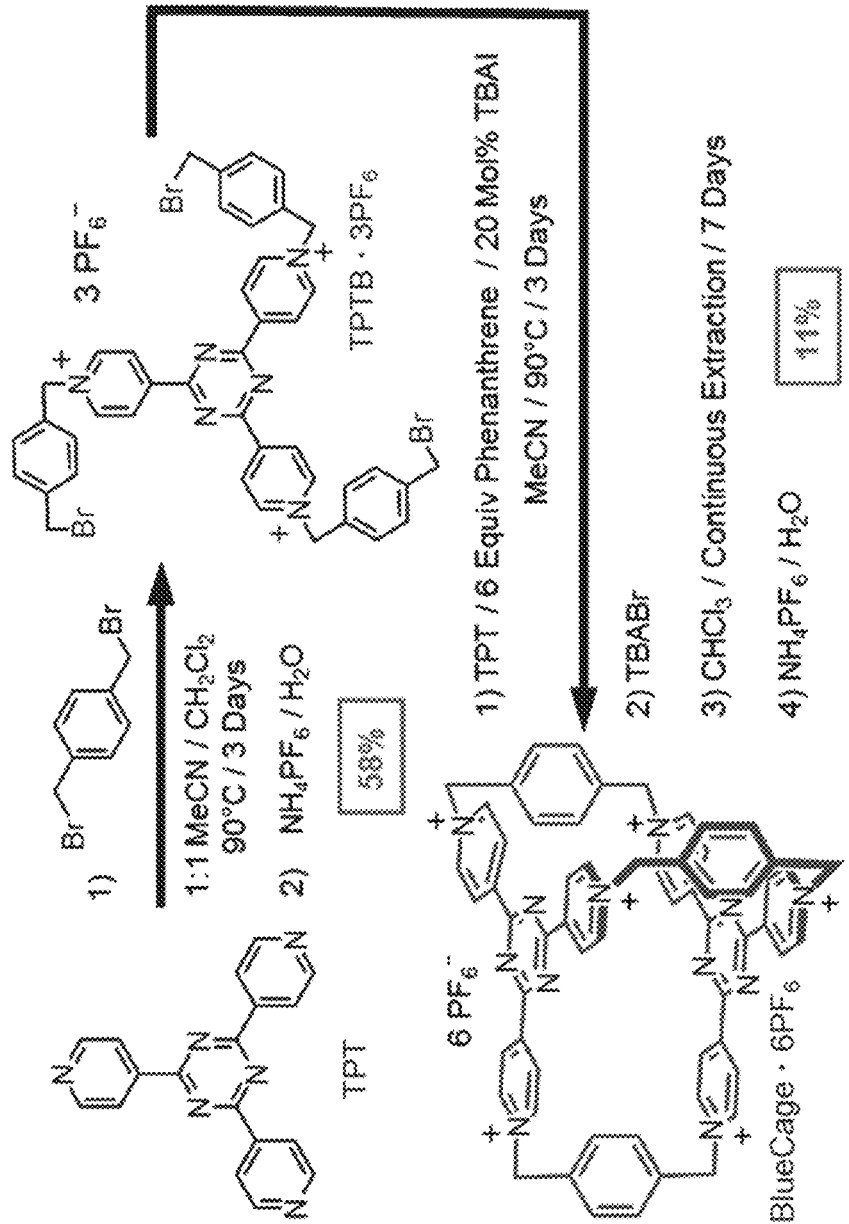
FIG. 3 depicts an exemplary scheme for the synthesis of BlueCage 6PF$_6$.

Scheme (2) presented in FIG. 3 provides an overview of the synthesis of the compound of formula (II).

The synthesis of TPTB.3 PF$_6$ was achieved according to Scheme (2A):

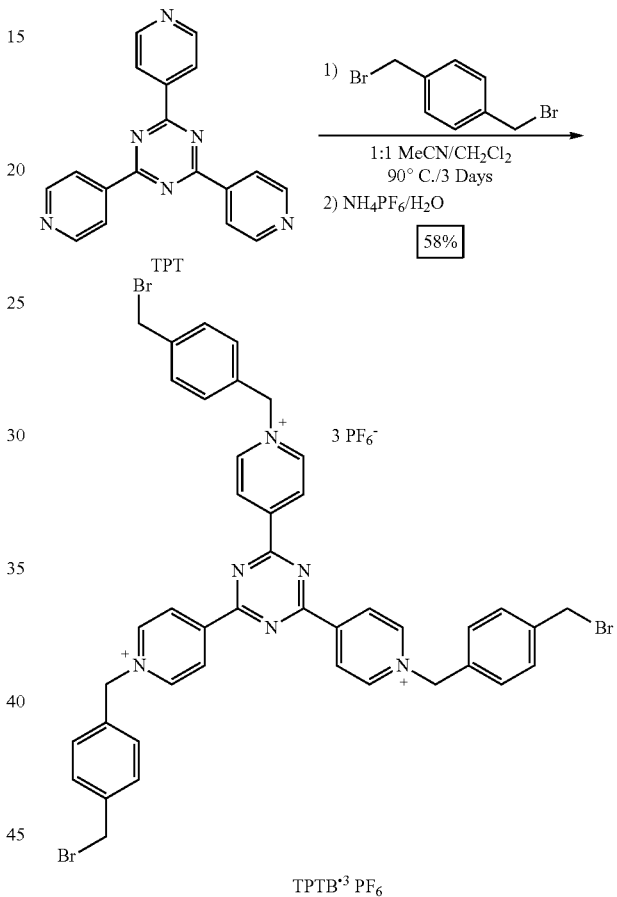

(Scheme (2A))

TPTB.3 PF$_6$. A solution of 1,4-bis(bromomethyl)benzene (7.98 g, 30.2 mmol) in 1:1 (v/v) MeCN—CH$_2$Cl$_2$ (120 mL) was heated to 90° C. in an atmosphere of argon and treated with solid TPT (703 mg, 2.25 mmol) in small portions. The mixture was stirred for 72 h, producing a yellow suspension over time. After cooling to room temperature, the suspension was diluted with CH$_2$Cl$_2$ (500 mL) and the solid was isolated by filtration. The filter cake was washed with copious amounts of CH$_2$Cl$_2$ and then triturated with MeOH (45 mL). The combined fractions were added to saturated aqueous NH$_4$PF$_6$ (500 mL), resulting in the precipitation of TPTB.3 PF$_6$ as a white solid (1.70 g, 1.31 mmol, 58%). $^1$H-NMR (500 MHz, CD$_3$CN) δ 9.25 (d, J=6.5 Hz, 6H), 9.08 (d, J=7 Hz, 6H), 7.57 (d, J=8 Hz, 6H), 7.53 (d, J=8.5 Hz, 6H), 5.88 (s, 6H), 4.62 (s, 6H). $^{13}$C-NMR (125 MHz, CD$_3$CN) δ 170.2, 150.5, 147.2, 141.4, 133.5, 131.5, 130.8, 128.6, 65.5, 33.5. HRMS (ESI) Calcd. for C$_{42}$H$_{36}$Br$_3$F$_{12}$N$_6$P$_2$: m/z=1152.9809 [M-PF$_6$]$^+$. found: 1152.9816.

The synthesis of BlueCage·6PF$_6$ was achieved according to Scheme (2B):

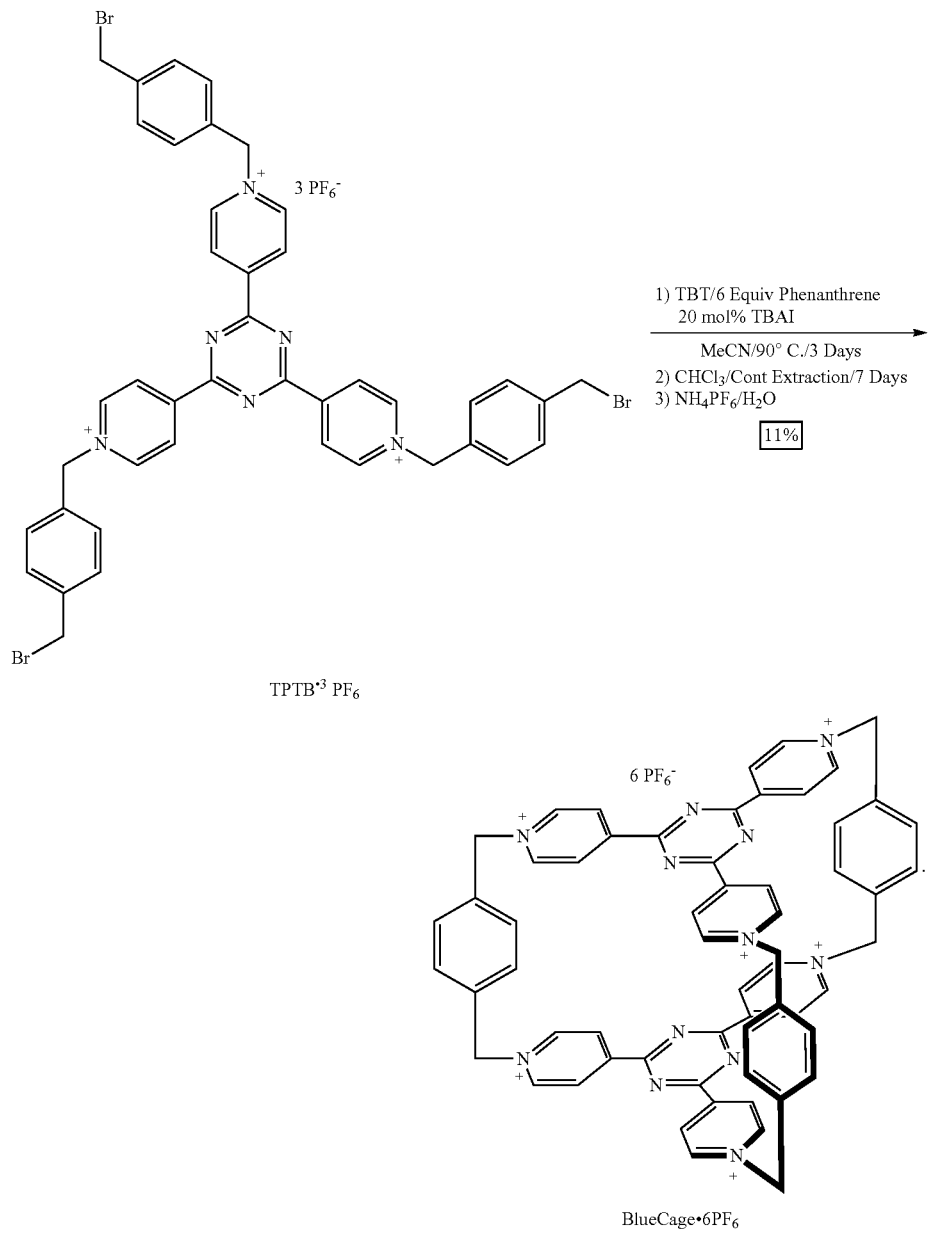

An intimate mixture of TPTB·3PF$_6$ (1.70 g, 1.31 mmol), 2,4,6-tris(4-pyridyl)-1,3,5-triazine (408 mg, 1.31 mmol), TBAI (97 mg, 0.26 mmol) and phenanthrene (2.10 g, 11.8 mmol) in MeCN (500 mL) was heated under reflux in an atmosphere of argon for 3 days. The reaction mixture was cooled to room temperature and treated with an excess of TBABr to precipitate the remaining solid that was collected by filtration. The filter cake was triturated with a minimum amount of H$_2$O and the combined aqueous fractions were subjected to continuous extraction with CHCl$_3$ for 7 days in order to remove the template. The aqueous phase was concentrated in vacuo and purified by preparative high-performance liquid chromatography, starting with H$_2$O containing 0.1% TFA as eluent, and adding up to 25% of MeCN/0.1% TFA. The combined fractions were concentrated under vacuum and treated with saturated aqueous NH$_4$PF$_6$ to furnish pure BlueCage·6PF$_6$ (257 mg, 143 μmol, 11%) as a white solid. $^1$H-NMR (500 MHz, CD$_3$CN) δ 9.06 (d, J=6.5 Hz, 12H), 9.05 (d, J=6.5 Hz, 12H), 7.63 (s, 12H), 5.82 (s, 12H). $^{13}$C-NMR (125 MHz, CD$_3$CN) δ 169.4, 150.4, 146.1, 136.8, 130.8, 128.7, 65.7. $^{19}$F-NMR (470 MHz, CD$_3$CN) δ −71.0 (d, J=706.9 Hz). $^{31}$P-NMR (162 MHz, CD$_3$CN) δ −143.59 (sept, J=708.6 Hz). HRMS (ESI) Calcd. for C$_{60}$H$_{48}$F$_{24}$N$_{12}$P$_4$: m/z=758.1341 [M−2PF$_6$]$^{2+}$. found: 758.1346.

The anion exchange of BlueCage·6PF$_6$ with Na[BArF] to give BlueCage·6BArF was achieved according to Scheme (2C):

(Scheme (2C))

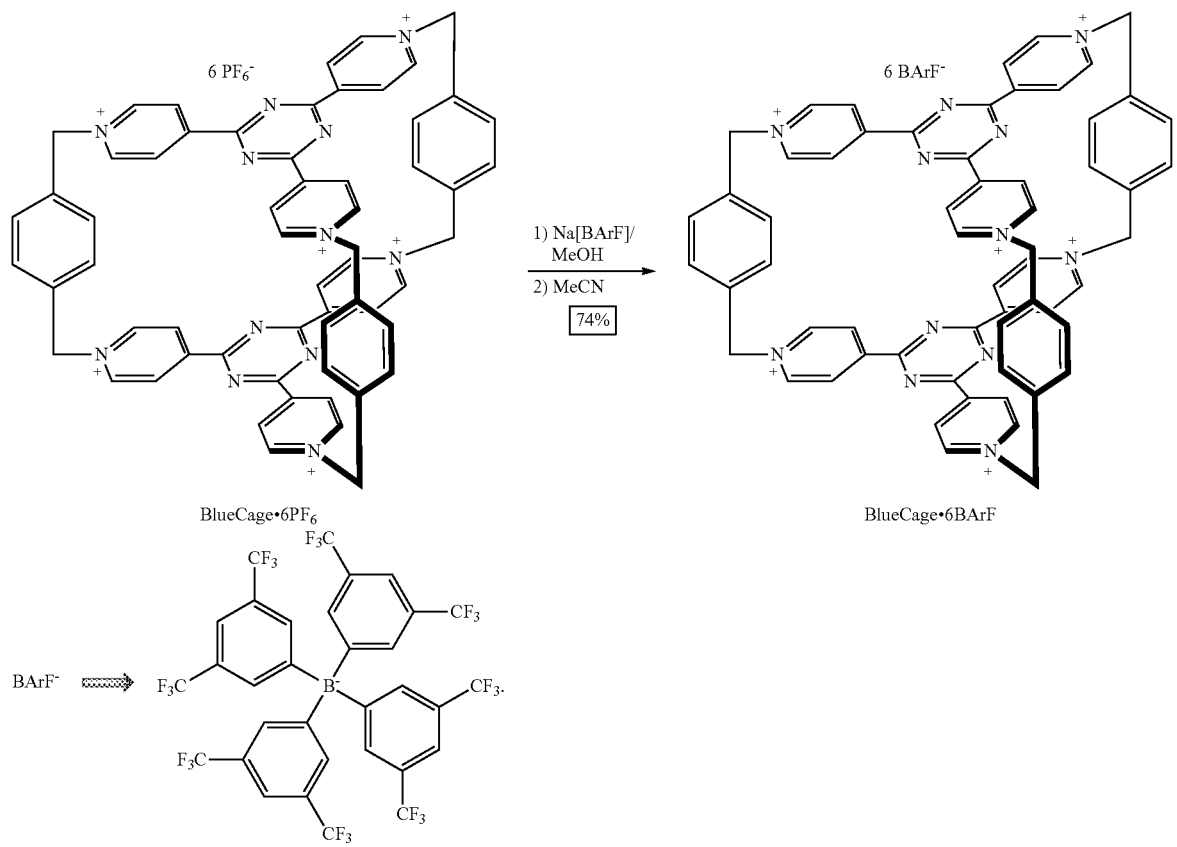

BlueCage·6BArF. A solution of BlueCage·6PF$_6$ (40 mg, 22 μmol) in MeCN (2 mL) was treated with an excess of TBACl to precipitate the chloride salt, which was collected by centrifugation. The solid was washed many times with MeCN, dissolved in MeOH, and treated with Na[BArF] (117 mg, 132 μmol). The solution was evaporated and the residue was taken up in MeCN and passed through a submicron filter. The mixture was concentrated under vacuum and the resulting viscous oil was triturated repeatedly with a minimum amount of Et$_2$O to give BlueCage·6BArF (100 mg, 16.3 μmol, 74%) as a viscous oil that solidifies on standing. $^1$H-NMR (500 MHz, CD$_3$CN) δ 9.09 (d, J=6.5 Hz, 12H), 8.98 (d, J=6.5 Hz, 12H), 7.70 (s, 12H), 7.69 (m, 48H), 7.66 (s, 24H), 5.82 (s, 12H).

The anion exchange of ExCage·6PF$_6$ with Na[BArF] to give ExCage·6BArF was achieved according to Scheme (2D):

(Scheme (2D))

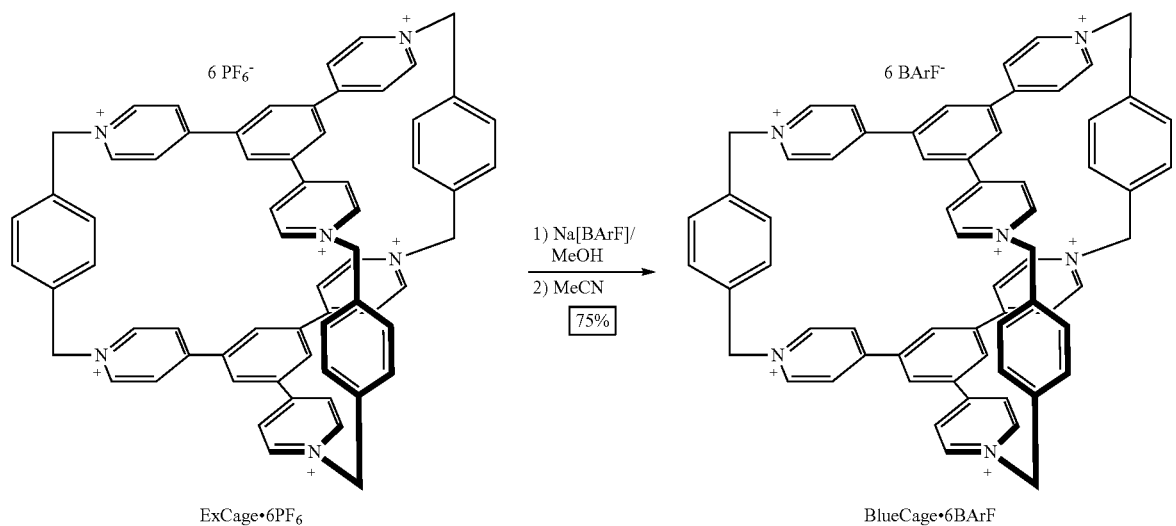

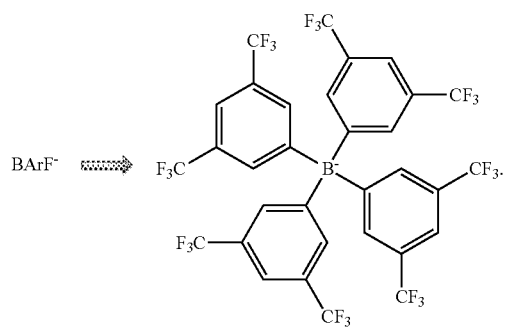

ExCage.6 BArF. A solution of ExCage.6 PF$_6$ (40 mg, 22 μmol) in MeCN (2 mL) was treated with an excess of TBACl to precipitate the chloride salt, which was collected by centrifugation. The solid was washed many times with MeCN, dissolved in MeOH, and treated with Na[BArF] (117 mg, 132 μmol). The solution was evaporated and the residue was taken up in MeCN and passed through a submicron filter. The mixture was concentrated under vacuum and the resulting viscous oil was triturated repeatedly with a minimum amount of Et$_2$O to give ExCage.6 BArF (102 mg, 16.7 μmol, 75%) as a viscous oil which solidifies on standing. $^1$H-NMR (500 MHz, CD$_3$CN) δ 8.78 (d, J=7.0 Hz, 12H), 8.38 (s, 6H), 8.28 (d, J=6.5 Hz, 12H), 7.69 (m, 48H), 7.59 (s, 24H), 5.75 (s, 12H).

The incorporation of coronene into BlueCage.6PF$_6$ to give Coronene ⊂ BlueCage.6PF$_6$ was achieved according to Scheme (2E):

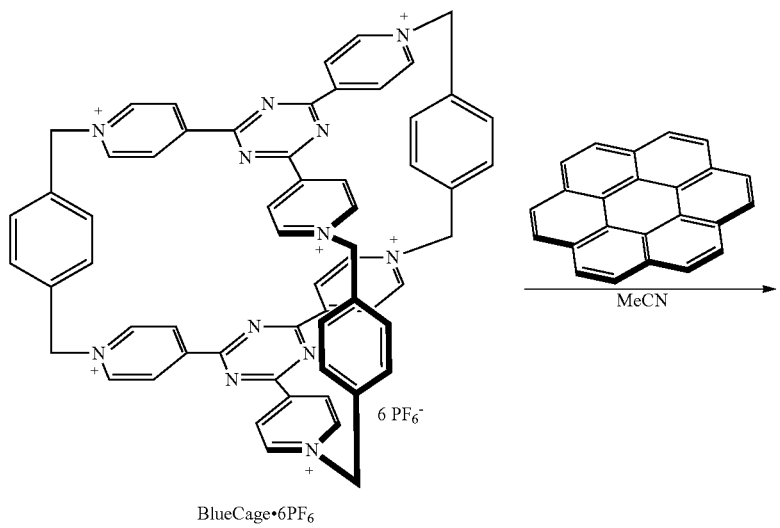

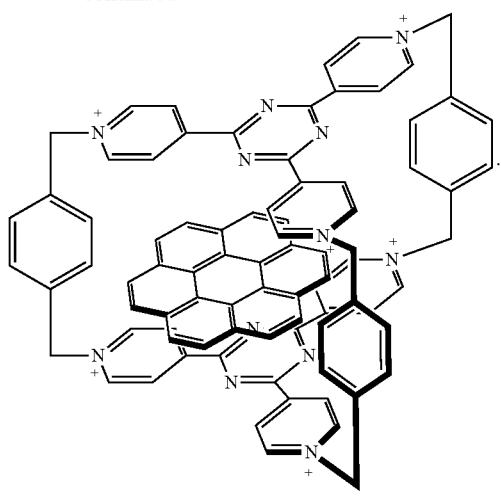

coronene⊂BlueCage·6PF$_6$

Coronene ⊂ BlueCage.6PF$_6$. One milligram (0.553 µmol) of BlueCage.6PF$_6$ in MeCN (1 mL) was treated with coronene (2 mg, 6.66 µmol), and sonicated for one min. The solution was passed through a submicron filter and subjected to vapor diffusion of iPr$_2$O, furnishing coronene ⊂ BlueCage.6PF$_6$ as deep purple crystals.

REFERENCES (1) (a) Dietrich, B.; Lehn, J.-M.; Sauvage, J.-P. *Tetrahedron Lett.* 1969, 2889; (b) Dietrich, B.; Lehn, J.-M.; Sauvage, J.-P. *Tetrahedron* 1973, 29, 1647; (c) Huang, R. H.; Faber, M. K.; Moeggenborg, K. J.; Ward, D. L.; Dye, J. L. *Nature* 1988, 331, 599; (d) von Hänisch, C.; Hampe, O.; Weigend, F.; Stahl, S. *Angew. Chem. Int. Ed.* 2007, 46, 4775; (e) Rupar, P. A.; Staroverov, V. N.; Baines, K. M. *Science* 2008, 322, 1360; (f) Hao, H.-G.; Zheng, X.-D.; Lu, T.-B. *Angew. Chem. Int. Ed.* 2010, 49, 8148; (g) Lopez, N.; Graham, D. J.; McGuire, R.; Alliger, G. E.; Shao-Horn, Y.; Cummins, C. C.; Nocera, D. G. *Science* 2012, 335, 450; (h) Wei, P.; Xia, B.; Zhang, Y.; Yu, Y.; Yan, X. *Chem. Commun.* 2014, 50, 3973.

(2) (a) Cram, D. J.; Kaneda, T.; Helgeson, R. C.; Brown, S. B.; Knobler, C. B.; Maverick, E.; Trueblood, K. N. *J. Am. Chem. Soc.* 1985, 107, 3645; (b) Cram, D. J.; Lein, G. M. *J. Am. Chem. Soc.* 1985, 107, 3657; (c) Bryant, J. A.; Ho, S. P.; Knobler, C. B.; Cram, D. J. *J. Am. Chem. Soc.* 1990, 112, 5837; (d) Mitjaville, J.; Caminade, A.-M.; Mathieu, R.; Majoral, J.-P. *J. Am. Chem. Soc.* 1994, 116, 5007; (e) Yi, H.-P.; Wu, J.; Ding, K.-L.; Jiang, X.-K.; Li, Z.-T. *J. Org. Chem.* 2007, 72, 870; (f) Skowronek, P.; Gawronski, J. *Org. Lett.* 2008, 10, 4755; (g) Giri, N.; Davidson, C. E.; Melaugh, G.; Del Pópolo, M. G.; Jones, J. T. A.; Hasell, T.; Cooper, A. I.; Horton, P. N.; Hursthouse, M. B.; James, S. L. *Chem. Sci.* 2012, 3, 2153.

(3) (a) Cram, D. J.; Karbach, S.; Kim, Y. H.; Baczynskyj, L.; Kalleymeyn, G. W. *J. Am. Chem. Soc.* 1985, 107, 2575; (b) Cram, D. J.; Karbach, S.; Kim, Y. H.; Baczynskyj, L.; Marti, K.; Sampson, R. M.; Kelleymeyn, G. W. *J. Am. Chem. Soc.* 1988, 110, 2554; (c) Sherman, J. C.; Cram, D. J. *J. Am. Chem. Soc.* 1989, 111, 4527; (d) Jasat, A.; Sherman, J. C. *Chem. Rev.* 1999, 99; (e) Roach, P.; Warmuth, R. *Angew. Chem. Int. Ed.* 2003, 42, 3039; (f) Makeiff, D. A.; Sherman, J. C. *J. Am. Chem. Soc.* 2005, 127, 12363; (g) Ihm, C.; Jo, E.; Kim, J.; Paek, K. *Angew. Chem. Int. Ed.* 2006, 45, 20569; (h) Chen, J. Y.-C.; Jayaraj, N.; Jockusch, S.; Ottaviani, M. F.; Ramamurthy, V.; Turro, N. J. *J. Am. Chem. Soc.* 2008, 130, 7206; (i) Srinivasan, K.; Gibb, B. C. *Chem. Commun.* 2008, 38, 4640; (j) Wang, H.; Liu, F.; Helgeson, R. C.; Houk, K. N. *Angew. Chem. Int. Ed.* 2013, 52, 655.

(4) (a) Cram, D. J.; Tanner, M. E.; Knobler, C. B. *J. Am. Chem. Soc.* 1991, 113, 7717; (b) Cram, D. J.; Jaeger, R.; Deshayes, K. *J. Am. Chem. Soc.* 1993, 115, 10111; (c) Makeiff, D. A.; Pope, D. J.; Sherman, J. C. *J. Am. Chem. Soc.* 2000, 122, 1337; (d) Warmuth, R.; Yoon, J. *Acc. Chem. Res.* 2001, 34, 95; (e) Warmuth, R.; Makowiec, S. *J. Am. Chem. Soc.* 2007, 129, 1233; (f) Lu, Z.; Moss, R. A.; Warmuth, R.; Krogh-Jespersen, K. *J. Phys. Chem. A* 2011, 115, 13799; (g) Li, M.-J.; Huang, C.-H.; Lai, C.-C.; Chiu, S.-H. *Org. Lett.* 2012, 14, 6146; (h) Lin, Z.; Sun, J.; Efremovska, B.; Warmuth, R. *Chemistry* 2012, 18, 12864.

(5) (a) Cram, D. J.; Tanner, M. E.; Knobler, C. B. *J. Am. Chem. Soc.* 1991, 113, 7717; (b) Cram, D. J. *Nature* 1992, 356, 29; (c) Cram, D. J.; Cram, J. M. *Container Molecules and their Guests.* In *Monographs in Supramolecular Chemistry*; Ed. Stoddart, J. F. Royal Society of Chemistry, Cambridge, 1994. Just as when cryptands form complexes, they are called cryptates, spherands, carcerands, and hemicarcerands are referred to as spheraplexes, carceplexes, and hemicarceplexes, respectively.

(6) (a) Barnes, J. C.; Juríček, M.; Strutt, N. L.; Frasconi, M.; Sampath, S.; Giesener, M. A.; McGrier, P. L; Bruns, C. J.; Stern, C. L.; Sarjeant, A. A.; Stoddart, J. F. *J. Am. Chem. Soc.* 2013, 135, 183; (b) Juríček, M.; Barnes, J. C.; Dale, E. J.; Liu, W.-G.; Strutt, N. L.; Bruns, C. J.; Vermeulen, N. A.; Ghooray, K. C.; Sarjeant, A. A.; Stern, C. L.; Botros, Y. Y.; Goddard III, W. A.; Stoddart, J. F. *J. Am. Chem. Soc.* 2013, 135, 12736; (c) Barnes, J. C.; Juríček, M.; Vermeulen, N. A.; Dale, E. J.; Stoddart, J. F. *J. Org. Chem.* 2013, 78, 11962.

(7) (a) Anderson, S.; Anderson, H. L.; Sanders, J. K. M.; *Acc. Chem. Res.* 1993, 26, 469; (b) Cacciapaglia, R.; Mandolini, L. *Chem. Soc. Rev.* 1993, 22, 221; (c) Hoss, R.; Vögtle, F. *Angew. Chem. Int. Ed. Engl.* 1994, 33, 375; (d) Hubin, T. J.; Busch, D. H. *Coord. Chem. Rev.* 2000, 200, 5; (e) Meyer, C. D.; Joiner, C. S.; Stoddart, J. F. *Chem. Soc. Rev.* 2007, 36, 1705; (f) Crowley, J. D.; Goldup, S. M.; Lee, A. L.; Leigh, D. A.; McBurney, R. T. *Chem. Soc. Rev.* 2009, 38, 1530.

(8) Anderson, H. L.; Anderson, S.; Sanders, J. K. M. *J. Chem. Soc. Perkin. Trans.* 1995, 2231-2245.

(9) Gries, W.-K.; Günther, E.; Hünig, S. *Liebigs Ann. Chem.* 1991, 1021-1028.

(10) Schmittel, M.; He, B.; Mal, P. *Org. Lett.* 2008, 10, 2513-2516.

Dale E J, Vermeulen N A, Thomas A A, Barnes J C, Juriček M, Blackburn A K, Strutt N L, Sarjeant A A, Stern C L, Denmark S E, Stoddart J F, "ExCage," *J. Am. Chem. Soc.* 136:10669-82 (2014).

Hafezi N, Holcroft J M, Hartlieb K J, Dale E J, Vermeulen N A, Stern C L, Sarjeant A A, Stoddart J F, "Modulating the binding of polycyclic aromatic hydrocarbons inside a hexacationic cage by anion-π interactions," *Angew. Chem. Int. Ed. Engl.* 54:456-61 (2015).

All of the patents, patent applications, patent application publications and other publications recited herein are hereby incorporated by reference as if set forth in their entirety.

The present invention has been described in connection with what are presently considered to be the most practical and preferred embodiments. However, the invention has been presented by way of illustration and is not intended to be limited to the disclosed embodiments. Accordingly, one of skill in the art will realize that the invention is intended to encompass all modifications and alternative arrangements within the spirit and scope of the invention as set forth in the appended claims.

The invention claimed is:

1. A compound salt of formula (I):

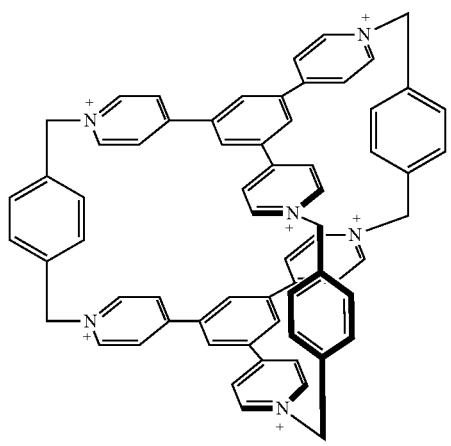

and $PF_6^-$.

2. A separation medium consisting of the compound salt according to claim 1.

3. A method of separating a polycyclic aromatic hydrocarbon (PAH) compound from a solvent comprising the PAH compound, comprising:

contacting the solvent comprising the PAH compound with a compound salt of formula (I):

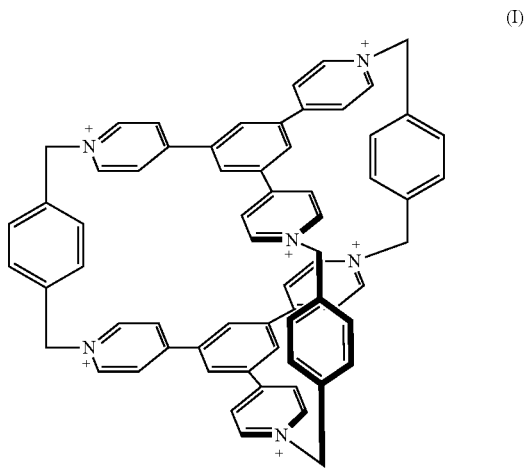

and $PF_6^-$.

4. The method of claim 3, wherein the solvent is selected from an aqueous or organic solvent.

5. The method of claim 3, wherein the PAH compound consists of a planar PAH compound.

6. The method of claim 5, wherein the PAH compound is naphthalene.

* * * * *